(12) United States Patent
Pennell et al.

(10) Patent No.: US 9,907,816 B2
(45) Date of Patent: *Mar. 6, 2018

(54) WATER-INSOLUBLE, IRON-CONTAINING MIXED METAL, GRANULAR MATERIAL

(71) Applicant: OPKO IRELAND GLOBAL HOLDINGS, LTD., Grand Cayman (KY)

(72) Inventors: Ruth Diane Pennell, Wirral (GB); Maurice Sydney Newton, Sandbacj (GB); James David Morrison, Norwich (GB); Alexis John Toft, Warrington (GB); Nigel Peter Rhodes, Warrington (GB)

(73) Assignee: OPKO IRELAND GLOBAL HOLDINGS, LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/603,084

(22) Filed: Jan. 22, 2015

(65) Prior Publication Data
US 2015/0132407 A1    May 14, 2015

Related U.S. Application Data

(63) Continuation of application No. 12/162,914, filed as application No. PCT/GB2007/000308 on Jan. 30, 2007, now Pat. No. 9,168,270.

(30) Foreign Application Priority Data

Jan. 31, 2006   (GB) ..................... 601899.8
Feb. 28, 2006   (GB) ..................... 603984.6

(51) Int. Cl.
| | |
|---|---|
| *A61K 33/06* | (2006.01) |
| *A61K 9/16* | (2006.01) |
| *A61K 9/20* | (2006.01) |
| *A61K 9/28* | (2006.01) |
| *A61K 33/24* | (2006.01) |
| *A61K 33/26* | (2006.01) |

(52) U.S. Cl.
CPC ............... *A61K 33/06* (2013.01); *A61K 9/16* (2013.01); *A61K 9/1611* (2013.01); *A61K 9/1635* (2013.01); *A61K 9/1652* (2013.01); *A61K 9/2077* (2013.01); *A61K 9/2846* (2013.01); *A61K 9/2866* (2013.01); *A61K 33/24* (2013.01); *A61K 33/26* (2013.01)

(58) Field of Classification Search
None
See application file for complete search history.

(56) References Cited

U.S. PATENT DOCUMENTS

| | | |
|---|---|---|
| 2,222,924 A | 11/1940 | Weiss |
| 2,812,344 A | 11/1957 | Oroshnik |
| 3,101,270 A | 8/1963 | Evans et al. |
| 3,395,211 A | 7/1968 | Wielich |
| 3,650,704 A | 3/1972 | Kumura et al. |
| 3,743,098 A | 7/1973 | Martinez |
| 3,796,792 A | 3/1974 | Miyata et al. |
| 3,879,523 A | 4/1975 | Miyata et al. |
| 3,984,392 A | 10/1976 | van der Veen et al. |
| 4,192,900 A | 3/1980 | Cheng |
| 4,254,099 A | 3/1981 | Asmussen et al. |
| 4,351,814 A | 9/1982 | Miyata et al. |
| 4,370,280 A | 1/1983 | Oediger et al. |
| 4,415,555 A | 11/1983 | Anabuki et al. |
| 4,458,026 A | 7/1984 | Reichle |
| 4,514,389 A | 4/1985 | Miyata |
| 4,566,986 A | 1/1986 | Waldmann |
| 4,582,705 A | 4/1986 | Primes et al. |
| 4,609,543 A | 9/1986 | Morris et al. |

(Continued)

FOREIGN PATENT DOCUMENTS

| | | |
|---|---|---|
| CA | 1198674 A1 | 12/1985 |
| DE | 2061136 A1 | 7/1971 |

(Continued)

OTHER PUBLICATIONS

Labajos et al. New layered double hydroxides with hydrotalcite structure containing Ni(II) and V(III), Journal of Materials Chemistry, 1999, 9, pp. 1033-1039.*

"Hydrothermal Methods" p. 108, IN: Duan et al. (eds.), Layered Double Hydroxides, Germany: Springer (2006).

Abramowitz et al., Serum alkaline phosphatase and phosphate and risk of mortality and hospitalization, Clin. J. Am. Soc. Nephrol., 5(6):1064-71 (2010).

Adachi-Pagano et al., Synthesis of Al-rich hydrotalcite-like compounds by using the urea hydrolysis reaction-control of size and morphology, J. Mater. Chem., 13(8):1988-93 (2003).

Adams et al., Formulation of a sterile surgical lubricant, J. Pharm. Pharmacol., 24 Suppl:178P (1972).

Albaaj et al., Hyperphosphataemia in renal failure: causes, consequences and current management, Drugs, 63(6):577-96 (2003).

Ambrogi et al., Intercalation compounds of hydrotalcite-like anionic clays with anti-inflammatory agents, II: Uptake of diclofenac for a controlled release formulation, AAPS PharmSciTech., 3(3):E26 (2002).

(Continued)

*Primary Examiner* — Melissa Fisher
(74) *Attorney, Agent, or Firm* — Marshall, Gerstein & Borun LLP

(57) ABSTRACT

There is provided a granular material comprising (i) at least 50% by weight based on the weight of the granular material of solid water-insoluble mixed metal compound capable of binding phosphate of formula (I): $M^{II}_{1-x}M^{III}_{x}(OH)_2 A^{n-}_{y} \cdot zH_2O$ (I) where $M^{II}$ is at least one of magnesium, calcium, lanthanum and cerium; $M^{III}$ is at least iron(III); $A^n$ is at least one n-valent anion; $x=\Sigma ny$, $0<x\leq 0.67$, $0<y\leq 1$, and $0\leq z<10$; (ii) from 3 to 12% by weight based on the weight of the granular material of non-chemically bound water, and (iii) no greater than 47% by weight based on the weight of the granular material of excipient.

19 Claims, No Drawings

(56) References Cited

U.S. PATENT DOCUMENTS

| | | |
|---|---|---|
| 4,629,626 A * | 12/1986 | Miyata .................. A61K 33/26 423/420.2 |
| 4,661,330 A | 4/1987 | Chane-Ching et al. |
| 4,689,219 A | 8/1987 | Sugden |
| 4,735,629 A | 4/1988 | Glemser et al. |
| 4,786,510 A | 11/1988 | Nakel et al. |
| 4,801,454 A | 1/1989 | Coveney |
| 4,970,079 A | 11/1990 | Hem et al. |
| 4,994,283 A | 2/1991 | Mehansho et al. |
| 5,002,747 A | 3/1991 | Le Loarer |
| 5,085,869 A | 2/1992 | Olthoff et al. |
| 5,112,604 A | 5/1992 | Beaurline et al. |
| 5,153,156 A | 10/1992 | Schutz et al. |
| 5,173,284 A | 12/1992 | Moisset et al. |
| 5,185,093 A | 2/1993 | Ichikawa et al. |
| 5,213,794 A | 5/1993 | Fritsch et al. |
| 5,246,899 A | 9/1993 | Bhattacharyya |
| 5,273,767 A | 12/1993 | Burgum |
| 5,300,302 A | 4/1994 | Tachon et al. |
| 5,506,248 A * | 4/1996 | Nikfar .................. A61K 9/2009 514/374 |
| 5,514,281 A | 5/1996 | Boos et al. |
| 5,525,305 A | 6/1996 | Minekus et al. |
| 5,571,336 A | 11/1996 | Wurzburger et al. |
| 5,651,997 A | 7/1997 | Makino et al. |
| 5,654,011 A | 8/1997 | Jackson et al. |
| 5,656,080 A | 8/1997 | Staniforth et al. |
| 5,817,340 A | 10/1998 | Roche et al. |
| 5,846,426 A | 12/1998 | Boos et al. |
| 5,968,976 A | 10/1999 | Murrer et al. |
| 6,028,023 A | 2/2000 | Vierheilig |
| 6,039,981 A | 3/2000 | Woo et al. |
| 6,103,126 A | 8/2000 | Boos et al. |
| 6,174,442 B1 | 1/2001 | Geisser et al. |
| 6,180,094 B1 * | 1/2001 | Sasaki .................. A61K 31/78 424/78.12 |
| 6,287,596 B1 | 9/2001 | Murakami et al. |
| 6,448,323 B1 | 9/2002 | Jordan et al. |
| 6,576,255 B1 | 6/2003 | Petereit et al. |
| 6,576,665 B2 | 6/2003 | Dennett, Jr. et al. |
| 6,596,311 B1 | 7/2003 | Dobetti |
| 6,696,087 B2 | 2/2004 | Matsuda et al. |
| 6,720,005 B1 | 4/2004 | Ayres |
| 6,733,780 B1 | 5/2004 | Tyler et al. |
| 6,749,864 B2 | 6/2004 | Makino et al. |
| 6,790,895 B2 | 9/2004 | Stelandre et al. |
| 6,794,367 B1 | 9/2004 | Tanida et al. |
| 6,926,912 B1 | 8/2005 | Roberts et al. |
| 7,259,192 B2 | 8/2007 | Liu et al. |
| 7,300,670 B2 | 11/2007 | Venus et al. |
| 7,799,351 B2 | 9/2010 | Roberts et al. |
| 8,568,792 B2 | 10/2013 | Roberts et al. |
| 9,168,270 B2 | 10/2015 | Pennel et al. |
| 9,314,481 B2 | 4/2016 | Applewhite et al. |
| 2002/0122786 A1 | 9/2002 | Matsuda et al. |
| 2003/0150249 A1 | 8/2003 | Gillman et al. |
| 2003/0185886 A1 | 10/2003 | Lee et al. |
| 2004/0022872 A1 | 2/2004 | Sofue et al. |
| 2004/0105896 A1 | 6/2004 | Roberts et al. |
| 2004/0247696 A1 | 12/2004 | Antelman |
| 2005/0170014 A1 * | 8/2005 | Krishnan ............. A61K 9/2009 424/646 |
| 2005/0260271 A1 | 11/2005 | Bringley |
| 2005/0266071 A1 | 12/2005 | Olmstead et al. |
| 2006/0177415 A1 | 8/2006 | Burke |
| 2007/0107637 A1 | 5/2007 | Gambin et al. |
| 2008/0187602 A1 | 8/2008 | Ferdinando et al. |
| 2008/0206358 A1 | 8/2008 | Newton et al. |
| 2009/0162658 A1 | 6/2009 | Wolk et al. |
| 2009/0175959 A1 | 7/2009 | Bando et al. |
| 2009/0317459 A1 | 12/2009 | Pennel et al. |
| 2010/0203152 A1 | 8/2010 | Newton et al. |
| 2010/0215770 A1 | 8/2010 | Newton et al. |
| 2011/0014301 A1 | 1/2011 | Roberts et al. |
| 2012/0093943 A1 | 4/2012 | Newton et al. |
| 2012/0201864 A1 | 8/2012 | Applewhite et al. |
| 2013/0323325 A1 | 12/2013 | Applewhite et al. |
| 2015/0132407 A1 | 5/2015 | Pennel et al. |

FOREIGN PATENT DOCUMENTS

| | | |
|---|---|---|
| DE | 3346943 A1 | 7/1985 |
| DE | 3402878 A1 | 8/1985 |
| DE | 3801382 A1 | 8/1989 |
| EP | 0050792 A1 | 5/1982 |
| EP | 0134936 A1 | 3/1985 |
| EP | 0146410 A2 | 6/1985 |
| EP | 0150792 A2 | 8/1985 |
| EP | 0368420 A2 | 5/1990 |
| EP | 0577294 A2 | 1/1994 |
| EP | 0638313 A1 | 2/1995 |
| EP | 1304104 A2 | 4/2003 |
| EP | 1413197 A2 | 4/2004 |
| EP | 1707178 A1 | 10/2006 |
| EP | 1932808 A1 | 6/2008 |
| EP | 1946750 A1 | 7/2008 |
| ES | 2018952 A6 | 5/1991 |
| FR | 1214473 A | 4/1960 |
| FR | 2254556 A1 | 7/1975 |
| GB | 1336866 A | 11/1973 |
| GB | 1378830 A | 12/1974 |
| GB | 2031395 A | 4/1980 |
| GB | 2254556 A | 10/1992 |
| HU | 173556 B | 6/1979 |
| HU | 201880 B | 1/1991 |
| IE | 63343 B1 | 4/1995 |
| IN | 192168 A1 | 3/2004 |
| JP | 61036222 A | 2/1986 |
| JP | 62145024 A | 6/1987 |
| JP | 3001114 A | 1/1991 |
| JP | 05155776 A | 6/1993 |
| JP | 05208816 A | 8/1993 |
| JP | 10059842 A | 3/1998 |
| JP | 10101569 A | 4/1998 |
| JP | 10236960 A | 9/1998 |
| JP | 3001114 B2 | 1/2000 |
| JP | 2000086537 A | 3/2000 |
| JP | 2001233619 A | 8/2001 |
| JP | 2001517633 A | 10/2001 |
| JP | 2004089760 A | 3/2004 |
| JP | 2007253030 A | 10/2007 |
| JP | 2008525292 A | 7/2008 |
| JP | 2009143798 A | 7/2009 |
| JP | 5105636 B2 | 12/2012 |
| PL | 200957 A1 | 4/1978 |
| PL | 189716 A1 | 3/1979 |
| PL | 189716 B1 | 6/1997 |
| PL | 200957 B1 | 11/1999 |
| SU | 414849 A1 | 9/1977 |
| WO | WO-91/18835 A1 | 12/1991 |
| WO | WO-92/01458 A1 | 2/1992 |
| WO | WO-93/22237 A1 | 11/1993 |
| WO | WO-94/09798 A1 | 5/1994 |
| WO | WO-95/11033 A1 | 4/1995 |
| WO | WO-95/29679 A1 | 11/1995 |
| WO | WO-96/30029 A1 | 10/1996 |
| WO | WO-97/11166 A1 | 3/1997 |
| WO | WO-97/22266 A1 | 6/1997 |
| WO | WO-97/26789 A1 | 7/1997 |
| WO | WO-97/48380 A1 | 12/1997 |
| WO | WO-99/15189 A1 | 4/1999 |
| WO | WO-99/44580 A1 | 9/1999 |
| WO | WO-00/32189 A1 | 6/2000 |
| WO | WO-01/27069 A1 | 4/2001 |
| WO | WO-01/49301 A1 | 7/2001 |
| WO | WO-03/013473 A1 | 2/2003 |
| WO | WO-03/017980 A1 | 3/2003 |
| WO | WO-03/028706 A1 | 4/2003 |
| WO | WO-03/072084 A1 | 9/2003 |
| WO | WO-03/092658 A1 | 11/2003 |
| WO | WO-2004/016553 A2 | 2/2004 |
| WO | WO-2004018094 A1 | 3/2004 |
| WO | WO-2005/009381 A2 | 2/2005 |
| WO | WO-2005/012194 A1 | 2/2005 |

(56) References Cited

FOREIGN PATENT DOCUMENTS

| WO | WO-2005/018651 A1 | 3/2005 |
|---|---|---|
| WO | WO-2005/027876 A1 | 3/2005 |
| WO | WO-2006/066341 A1 | 6/2006 |
| WO | WO 2006/085079 * | 8/2006 |
| WO | WO-2006/085079 A2 | 8/2006 |
| WO | WO-2007/074909 A1 | 7/2007 |
| WO | WO-2007/088343 A2 | 8/2007 |
| WO | WO-2007/135362 A2 | 11/2007 |
| WO | WO-2008/071747 A1 | 6/2008 |
| WO | WO-2008/129034 A1 | 10/2008 |
| WO | WO-2009/016349 A1 | 2/2009 |
| WO | WO-2009/050468 A1 | 4/2009 |

OTHER PUBLICATIONS

Ansel et al., Pharmaceutical Dosage Forms and Drug Delivery Systems, Chapters 1-8 (pp. 1-243) Lippincott, Williams & Wilkins (1999).
Aoshima et al., Glycerin fatty acid esters as a new lubricant of tablets, Int. J. Pharm., 293 (1-2):25-34 (2005).
Autissier et al., Relative in vitro efficacy of the phosphate binders lanthanum carbonate and sevelamer hydrochloride, J. Pharm. Sci., 96(10):2818-27 (2007).
Badawy et al., Effect of drug substance particle size on the characteristics of granulation manufactured in a high-shear mixer, AAPS PharmSciTech., 1(4):E33 (2000).
Badreddine et al.,Ion exchange of different phosphate ions into the zinc-aluminium-chloride layered double hydroxide, Materials Lett., 38(6): 391-5 (1999).
Barriga et al., Hydrotalcites as sorbent for 2,4,6-trinitrophenol: influence of the layer composition and interlayer anion, J. Mater. Chem., 12:1027-34 (2002).
Bejoy, Hydrotalcite: The Clay that Cures, Springer; Resonance, vol. 6 No. 2, pp. 57-61 (2001).
Bolhuis et al., Interaction of tablet disintegrants and magnesium strearate during mixing I: effect on tablet disintegration, J. Pharm. Sci., 70(12):1328-30 (1981).
Bolognini et al., Mg/Al mixed oxides prepared by coprecipitation and sol-gel routes: a comparison of their physico-chemical features and performances in m-cresol methylation, Microporous and Mesoporous Materials, 66:77-89 (2003).
Bothwell, Overview and mechanisms of iron regulation, Nutrition Rev., 53:237-45 (Sep. 1995).
Brauner, Das atomgewicht des lanthans, Zeitschrift fur Anorganische Chemie, 33(1):317-21 (1902).
Brouwers et al., Biopharmaceutical tests on antacids: in vitro and in vivo studies, Drugs Under Experiment. Clin. Res., 5:55-61 (1997).
Brouwers et al., De invioed van de toedieningsvorm op de weringsduur en op het pH-Bereik bij antacida: een in-vitro en in-vivo studie,Pharmaceutisch Weekblad, 111:1244-8 (1976) (abstract only).
Brouwers, Liquid Antacids, Pharmaceutisch Weekblad, 110:337-51 (1975) (abstract only).
Budavari et al. (eds.), The Merck Index, pp. 277, 331, and 917, Merck & Co. (1996).
Cargill et al., Chemical reactivity of aluminium-based pharmaceutical compounds used as phosphate-binders, J. Pharm. Pharmacol., 41:11-16 (1989).
Carlino, Chemistry between the sheets, Chemistry in Britain, pp. 59-62 (Sep. 1997).
Chatelet et al., Competition between monovalent and divalent anions for calcined and uncalcined hydrotalcite: anion exchange and adsorption sites, Colloids and Surfaces A: Physiochemical and Engineering Aspects, 111:167-75 (1996).
Chitrakar et al., Adsorption of phosphate from seawater on calcined MgMn-layered double hydroxides, J. Colloid Interface Sci., 290(1): 45-51 (2005).
Cook, Adaptation in iron metabolism, Am. J. Clin. Nutr., 51(2):301-8 (1990).

Das et al., Adsorption of phosphate by layered double hydroxides in aqueous solutions, Appl. Clay Sci., 32(3-4:252-60 (2006).
de Roy et al., "Layered double hydroxides: synthesis and post-synthesis modification", Chapter 1 (pp. 1-37) IN: Rives (ed)., Layered Double Hydroxides: Present and Future, Nova Science Pub Inc. (2001).
de Roy et al., Anionic Clays: Trends in Pillaring Chemistry, chapter 7, pp. 108-169 IN: Synthesis of Microporous Mateirals (1992).
del Arco et al., Effect of the Mg:Al ratio on borate (or silicate)/ nitrate exchange in hydrotalcite, J. Solid State Chem., 151(2):272-80 (2000).
del Arco et al., Surface and textural properties of hydrotalcite-like materials and their decomposition products, IN: Rouquerol et al. (eds.), Characterization of Porous Solids III, Studies in Surface Science and Catalysis, vol. 87, pp. 507-515 (1994).
Dewberry et al., "Lanthanum carbonate: A novel non-calcium containing phosphate binder", J Am Soc Nephrol, 8:A2610 (1997).
Drueke, Lanthanum carbonate as a first-line phosphate binder: the "cons", Semin. Dial., 20(4):329-32 (2007).
Emmett, A comparison of clinically useful phosphorus binders for patients with chronic kidney failure, Kidney Int.,66:S25-S32 (2004).
Entry for "obtainable", Collins English Dictionary, retrieved from the Internet at <http://www.collinsdictionary.com> on May 15, 2013.
Erickson et al., A study of structural memory effects in synthetic hydrotalcites using environmental SEM, Materials Lett., 59:226-9 (2005).
European Search Report for European application No. EP 06013811, dated Jun. 27, 2007.
Evans et al., "Structural Aspects of Layered Double Hydroxides" pp. 1-12, IN: Duan et al. (eds.), Layered Double Hydroxides, vol. 119, Springer (2006).
Evonik Industries AG, product information for Eudragit® E100, Eudragit® E POA and Eudragit® E 12,5; pp. 1-6 (Oct. 2011).
Fernandez et al., The effect of iron on the crystalline phases formed upon thermal decomposition of Mg—Al—Fe hydrotalcites, RCS Publishing: Journal of Materials Chemistry, 8(11):2507-14 (1998).
Ferreira et al., Thermal decomposition and structural reconstruction effect on Mg Fe based hydrocalcite compounds, J. Solid State Chem., 177:3058-69 (2004).
Forano, Environmental remediationinvolving layered double hydroxides, pp. 426-458, vol. 1, Elsevier Interface Science and Technology (2004).
Frost et al., Thermal decomposition of synthetic hydrotalcites reevesite and pyroaurite, J. Therm. Analysis Calorimetry, 76:217-25 (2004).
Goh et al., Application of layered double hydroxides for removal of oxyanions: a review, Water Res., 42:1343-68 (2008).
Grant et al. (eds.), Grant & Hackh's Chemical Dictionary, 5th edition, McGraw Hill, pp. 571 (1987).
Grubel et al., Interaction of an aluminum-magnesium containing antacid and gastric mucus: possible contribution to the cytoprotective function of antacids, Aliment. Pharmacol. Ther., 11(1):139-45 (1997).
Guillot et al., The use of magnesium-containing phosphate binders in patients with end-stage renal disease on maintenance hemodialysis, Nephron., 30(2):114-7 (1982).
Hansen et al., Formation of synthetic analogues of double metal-hydroxy carbonate minerals under controlled pH conditions: I. The synthesis of pyroaurite and reevesite, Clay Minerals, 25:161-79 (1990).
Hansen et al., Reduction of nitrate to ammonium by sulphate green rust: activation energy and reaction mechanism, Clay Minerals, 33:87-101 (1998).
Hansen et al., Synthesis and characterization of pyroaurite, Appl. Clay Sci., 10(1-2):5-19 (1995).
Hansen et al., The use of glycerol intercalates in the exchange of $CO_3^{2-}$ with $SO_4^{2-}$, $NO^{3-}$ or $C_L$- in pyroaurite-type compounds, Clay Minerals, 26:311-27 (1991).
Hashi et al., Preparation and properties of pyroaurite-like hydroxy minerals, Clays and Clay Minerals, 31(2):152-4 (1983).

(56) References Cited

OTHER PUBLICATIONS

He et al., Hydrothermal Methods, p. 108 IN: Duan et al. (eds.), Layered Double Hydroxides, Springer-Verlag Berlin Heidelberg (2006).

He et al., Preparation of Layered Double Hydroxides, Struct. Bond., 119:89-119 (2006).

Hibino et al., Calcination and rehydration behavior of Mg—Fe—CO3 hydrotalcite-like compounds, J. Materials Sci. Lett., 19(16):1403-5 (2000).

Hirahara et al., Synthesis and antacid property of Mg—Fe layered double hydroxide, Nendo Kagaku—J. Clay Sci. Soc. of Japan, 42(2):70-6 (2002).

Hollander et al., Antacids vs. placebos in peptic ulcer therapy: a controlled double-blind investigation, JAMA, 226(10):1181-5 (1973).

Hudson et al., Thermal conversion of a layered (Mg/Al) double hydroxide to the oxide, J. Mater. Chem., 5(2):323-9 (1995).

International Specialty Products, Pharmaceuticals Solid Dosage Forms, pp. 1-13 (2004).

Iranloye et al., Effects of compression force, particle size and lubricants on dissolution rate, J. Pharm. Sci., 67(4):535-9 (1978).

Ishimura et al., "Hyper- and Hypophosphataemia" pp. 149-158, IN: Morii et al. (eds.), Calcium in Internal Medicine, Springer (2002).

Kaplan et al., A preference study: calcium acetate tablets versus gelcaps in hemodialysis patients, Nephrol. Nurs. J., 29(4):363-5 (2002).

Kebler et al., Dynamic changes in serum phosphorus levels in diabetic ketoacidosis, Am. J. Med., 79(5):571-6 (1985).

Kokot et al., A rotating disk study on the rates of hydrotalcite dissolution at 25° C, Pharmazie, 48 (H4):287-9 (1993).

Konorev et al., Selection of the optimal antacid drug in clinical practice, Consilium Medicum, vol. 5, pp. 1-10 (2003).

Kostura et al., Rehydration of calcined Mg—Al hydrotalcite in acidified chloride-containing aqueous solution, Collect. Czech. Chem. Commun., 72:1284-94 (2007).

Kovanda et al., Thermal behavior of Ni-Mn layered double hydroxide and characterization of formed oxides, Solid State Sci., 5:1019-26 (2003).

Labajos et al., New layered double hydroxides with hydrotalcite structure containing Ni(II) and V(III), J. Materials Chem., 9:1033-9 (1999).

Larsson et al., Estimation of the Bioavailability of Iron and Phosphorus in Cereals using a Dynamic In Vitro Gastrointestinal Model, J. Sci. Food Agric., 74(1):99-106 (1997).

Lazaridis et al., Flotation of metal loaded clay anion exchangers, Part II: the case of chromates, Chemosphere, 42:373-8 (2001).

Lazaridis etal, Flotation of metal loaded clay anion exhcnagers Part I: the case of chromates, Chemosphere 42:373-8 (2001).

Lazaridis, Sorption removal of anions and cations in single batch systems by uncalcined and calcined Mg—Al—CO3 hydrotalcite, Water Air Soil Pollution, 146:127-39 (2003).

Leinonen et al., Physical and lubrication properties of magnesium stearate, J. Pharm. Sci., 81(12):1194-8 (1992).

Li et al., Enteric-coated layered double hydroxides as a controlled release drug delivery system, Int. J. Pharm., 287(1-2):89-95 (2004).

Li et al., Stoichiometric Synthesis of Pure MFe2O4 (M=Mg, Co, and Ni) Spinel Ferrites from Tailored Layered Double Hydroxide (Hydrotalcite-Like) Precursors, Chem. Mater., 16(8):1597-602 (2004).

Lin et al., Evaluation of buffering capacity and acid neutralizing-pH time profile of antacids, J. Formos. Med. Assoc., 97:704-10 (1998).

Linares et al., The influence of hydrotalcite and cancrinite type zeolite in acidic aspirin solutions, Microporous and Mesoporous Materials, 74:105-10 (2004).

Llewellyn et al., The binding of bile acids by hydrocalcite and other antacid preparations, Pharmaceutica Acta Helvetiae, 52(1/2):1-5 (1977).

Logham-Adham, Safety of new phosphate binders for chronic renal failure, Drug Safety, 26(15):1093-1115 (2003).

MacCara, Acid neutralization capacity of Canadian antacid formulations, Can. Med. Assoc. J., 132:523-7 (1985).

Marchi et al., Impregnation-induced memory effect of thermally activated layered double hydroxide, Appl. Clay Sci., 13:35-48 (1998).

McCance et al., Absorption and excretion of iron, The Lancet, pp. 680-684 (Sep. 18, 1937).

McIntyre et al., Iron-magnesium hydroxycarbonate (Alpharen): a novel non calcium containing phosphate binder for the treatment of hyperphosphataemia in chronic haemodialysis patients, Nephrol. Dial. Transplant., 22 (suppl 6): vi171, FP452 Poster Session Abstract (Jun. 22, 2007).

McIntyre et al., Iron-magnesium hydroxycarbonate (fermagate): a novel non-calcium-containing phosphate binder for the treatment of hyperphosphatemia in chronic hemodialysis patients, Clin. J. Am. Soc. Nephrol., 4(2):401-9 (2009).

Meng et al., Preparation and thermal decomposition of magnesium/iron (III) layered double hydroxide intercalated by hexacyanoferrate (III) ions, J. Mater. Sci., 39:4655-7 (2004).

Meng et al., Preparation of magnetic material containing MgFe2O4 spinel ferrite from a Mg—Fe(III) layered double hydroxide intercalated by hexacyanoferrate(III) ions, Mater.Chem. Phys., 86:1-4 (2004).

Merck Index, p. 969, entries 5694-707 (1996).

Merriam-Webster's Collegiate Dictionary—11th edition, entry for "prophylaxis" on p. 996 (2004).

Mesh to Micron Conversion chart, retrieved from the Internet at <http://www.shomegold.org/news/Mesh.htm>, accessed Sep. 27, 2012.

Miederer et al., Acid neutralization and bile acid binding capacity of hydrocalcite compared with other antacids: an in-vitro study, Chinese J. Digestive Diseases, 4(3):140-6 (2003).

Miyata et al., Physiochemical properties of synthetic hydrotalcites in relation to composition, Clays and Clay Minerals, 28(1):50-6 (1980).

Murthy et al., Effect of shear mixing on in vitro drug release of capsule formulations containing lubricants, J. Pharm. Sci., 66(9):1215-9 (1977).

Naylor et al., Use of gastro-intestinal model and gastroplus for the prediction of in vivo performance, Industrial Pharmacy, Dec. 2006, issue 12 p. 9-12.

Newman et al., Comparative study of some layered hydroxide salts containing exchangable interlayer anions, J. Solid State Chem., 148:26-40 (1999).

O'Donovan et al., Substitution of aluminium salts by magnesium salts in control of dialysis hyperphosphataemia, The Lancet, pp. 880-881 (Apr. 19, 1986).

Oe et al., Long-term use of magnesium hydroxide as a phosphate binder in patients on hemodialysis, Clin. Nephrol., 28(4):180-5 (1987).

Ookubo et al., Hydrotalcites as potential adsorbents of intestinal phosphate, J. Pharm. Sci., 81(11):1139-40 (1992).

Ookubo et al., Preparation and phosphate ion-exchange properties of a hydrotalcite-like compound, Langmuir, 9(5):1418-22 (1993).

Pesic et al., Thermal characteristics of a synthetic hydrotalcite like material, J. Mater. Chem., 2(10):1069-73 (1992).

Playle et al., The in vitro antacid and anti-pepsin activity of hydrotalcite, Pharm. Acta Helv., 49 Nr. 9/10: 298-302 (1974).

Powell et al., The chemistry between aluminum in the gastrointestinal lumen and its uptake and absorption, Proc. Nutrition Soc., 52:241-53 (1993).

Rajamathi et al., Reversable thermal behaviour of the layered double hydroxide of Mg with Al: mechanistic studies, J. Mater. Chem., 10:2754-7 (2000).

Raki et al., Preparation, Characterization, and Moessbauer Spectroscopy of Organic Anion Intercalated Pyroaurite-like Layered Double Hydroxides, Chem. Mater., 7(1):221-4 (1995).

Rankin et al., The development and in-vitro evaluation of novel mixed metal hydroxy-carbonate compounds as phosphate binders, J. Pharm. Pharmacol., 53:361-9 (2001).

Reichle, Synthesis of anionic clay minerals (mixed metal hydroxides, hydrotalcite), Solid State Ionics, 22(1):135-41 (1986).

(56) References Cited

OTHER PUBLICATIONS

Remuzzi et al., Hematologic consequences of renal failure, Chapter 50, pp. 2079-2102 IN: Rose, Pathophysiology of Renal Disease, McGraw-Hill (1987).
Rives, Study of Layered Double Hydroxides by Thermal Methods, chapter 4, pp. 116-133 IN: Rives (ed.), Layered Double Hydroxides: Present and Future, Nova Science Pub Inc. (2001).
Robolot et al., Effect of lubricant level and applied copressional pressure on surface friction of tablets, J. Pharm. Sci., 74(6):697-9 (1985).
Rodriguez-Benot et al., Mild hyperphosphatemia and mortality in hemodialysis patients, Am. J. Kidney Dis., 46(1):68-77 (2005).
Rubinstein et al., The effect of granule size on the in vitro and in vivo properties of bendrofluazide tablets 5mg, Pharm. Acta Helv., 52 (1/2): 5-10 (1977).
Rudnic et al., Oral Solid Dosage Forms, chapter 45, pp. 858-890 IN: Gennaro (ed.), Remington: The Science and Practice of Pharmacy, 20th ed., Lippincott Williams & Wilkins (2000).
Sato et al., Adsorption of various anions by magnesium aluminum oxide Mg(0.7)Al(0.3)O(1.15), Ind. Eng. Chem. Prod. Res. Dev., 25:89-92 (1986).
Sato et al., Causticization of sodium carbonate with rock-salt-type magnesium aluminium oxide formed by the thermal decomposition of hydrotalcite-like layered double hydroxide, J. Chem. Tech. Biotechnol., 57:137-40 (1993).
Schwarz et al., Association of disorders in mineral metabolism with progression of chronic kidney disease, Clin. J. Am. Soc. Nephrol., 1(4):825-31 (2006).
Seida et al., Removal of phosphate by layered double hydroxides containing iron, Water Res., 36:1305-12 (2002).
Sheikh et al., Reducation of dietary phosphorus absorption by phosphorous binders: A theoretical, in vitro, and in vivo study, J. Clin. Invest., 83:66-73 (1989).
Shen et al., Preparation and characterization of Fe/MgO catalysts obtained from hydrotalcite-like compounds, Catalysis Today, 30(1-3):77-82 (1996).
Shin et al., Phosphorus removal by hydrotalcite-like compounds (HTLcs), Water Sci. Technol., 34(1-2):161-8 (1996).
Sigma-Aldrich product information for Iron(III) nitrate nonanhydrate, retrieved from the Internet: <http:www.sigmaaldrich.com> on Jun. 11, 2012 (one page).
Spengler et al., Cross-linked iron dextran is an efficient oral phosphate binder in the rat, Nephrol. Dial. Transplant., 11(5):808-12 (1996).
Stamatakis et al., Influence of pH on in vitro disintegration of phosphate binders, Am. J. Kidney Dis., 32(5):808-12 (1998).
Suren, Evaluation of lubricants in the development of tablet formulation, Dansk TIDSskr. Farm 45, pp. 331-338 (1971).
Tezuka et al, The Synthesis and Phosphate Adsorptive Properties of Mg(II)-Mn(III) Layered Double Hydroxides and Their Heat-Treated Materials, Bull Chem. Soc. Jpn. 2004, 77:2101-7 (2004).
The National Kidney Foundation Kidney Disease Quality Outcomes Initiative, Clinical Practice Guidelines for Bone Metabolism and Disease in Chronic Disease, Guide 5 pp. 1, pt. 5.5 (2003).
Tichit et al., Catalysis by hydrotalcites and related materials, Cattech, 7(6):206-17 (2003).
Titulaer et al., The formation of ice between hydrotalcite particles measured by thermoporometry, Clay Minerals, 31(2):263-77 (1996).
Toth et al., Nano-scaled inorganic/biopolymer composites: molecular modeling vistas, AIChE Annual Meeting (2005).
Toth et al., Structure and energetics of biocompatible polymer nanocomposite systems: a molecular dynamics study, Biomacromolecules, 7:1714-9 (2006).
Trifiro et al, "Hydrotalcite-like Anionic Clays (Layered Double Hydroxides)", vol. 7, chapter 8, pp. 251-291, IN: Alberti et al. (eds.) Comprehensive Supramolecular Chemistry, Pergamon, Oxford (1996).
Tsuji et al., Hydrotalcites with an extended $Al^{3+}$-substitution: synthesis, simultaneous TG-DTA-MS study, and their $CO_2$ adsorption behaviors, J. Mater. Res., 8(5):1137-42 (1993).
Ulibarri et al., Kinetics of the thermal dehydration of some layered hydroxycarbonates, Thermochimica Acta, 135:231-6 (1998).
USANA Technical Bulletin, Tablet Excipients, Jun. 1999.
Van Der Voet et al., Intestinal absorption of aluminium from antacids: a comparison between hydrotalcite and algeldrate, Clin. Tech., 24(6):545-3 (1986).
Vatier et al., Antacid activity of calcium carbonate and hydrotalcite tablets, Arzneim-Forsch/Drug Res., 44(4):514-8 (1994).
Vitkova et al., The use of some hydrophobic substances in tablet technology, Milan Chilabala, Acta Pharamceutica Hungaria, 68:336-44 (1998).
Written Opinion for PCT/GB2007/000308, Nov. 30, 2007.
Wrong et al., Sevelamer and other anion-exchange resins in the prevention and treatment of hyperphosphataemia in chronic renal failure, Nephron. Physiol., 107:17-33 (2007).
Zhang et al., Phosphorous anion exchange characteristic of a pyroaurite-like compound, Inorg. Mater., 4:132-8 (1997).
Zhang et al., Synthesis and characterization of a novel nanoscale magnetic solid base catalyst involving a layered double hydroxide supported on a ferrite core, J. Solid State Chem., 177:772-80 (2004).
Zhang et al., Synthesis of Mg/Fe pyroaurite-like compounds and their anion-exchange characteristics, Inorg. Mater., 2(259):480-5 (1995).
Zhao et al., Preparation of layered double-hydroxide nanomaterials with a uniform crystalite size using a new method involving separate nucleation and aging steps, Chem. Mater., 14(10):4286-91 (2002).
Zhu et al., Adsorption of phosphate by hydrotalcite and its calcined product, Acta Mineralogica Sinica, 25(1):27-32 (2005).
Zhu et al., Different Mg to Fe ratios in the mixed metal MgFe hydroxy-carbonate compounds and the effect on phosphate binding compared with established phosphate binders, J. Pharm. Sci., 91(1):53-66 (2002).

* cited by examiner

WATER-INSOLUBLE, IRON-CONTAINING MIXED METAL, GRANULAR MATERIAL

CROSS-REFERENCE TO RELATED APPLICATION

This application is a continuation of U.S. patent application Ser. No. 12/162,914, which is a U.S. national phase of International Patent Application No. PCT/GB2007/000308 filed Jan. 30, 2007, which in turn claims the priority benefit of Great Britain Patent Application No. GB0601899.8 filed Jan. 31, 2006, and Great Britain Patent Application No. GB0603984.6 filed Feb. 28, 2006, the respective disclosure of which are each incorporated herein by reference in their entireties.

FIELD

The present invention relates to granules containing water-insoluble inorganic solids, particularly mixed metal compounds, having pharmaceutical activity, as phosphate binders. It also extends to methods of manufacture of the granules and their use in unit doses for oral administration.

BACKGROUND

Various ailments may lead to high phosphate concentrations in the blood in animals, particularly warm-blooded animals such as humans. This can lead to a number of physiological problems, such as deposition of calcium phosphate.

In patients with kidney failure who are being treated by regular haemodialysis, phosphate concentrations in the blood plasma can rise dramatically and this condition, known as hyperphosphataemia, can result in calcium phosphate deposition in soft tissue. Plasma phosphate levels may be reduced by oral intake of inorganic and organic phosphate binders.

Classes of inorganic solid phosphate binders are disclosed in WO 99/15189. These include alkali treated inorganic sulphates, such as calcium sulphate, and mixed metal compounds which are substantially free from aluminium and which have a phosphate binding capacity of at least 30% by weight of the total weight of phosphate present, over a pH range of from 2-8, as measured by the phosphate binding test as described therein. The inorganic solids are water insoluble and are primarily intended for oral administration.

Typically such mixed metal compounds may contain iron (III) and at least one of magnesium, calcium, lanthanum and cerium. Preferably they also contain at least one of hydroxyl and carbonate anions and optionally additionally, at least one of sulphate, chloride and oxide.

Mixed metal compounds such as described in WO 99/15189 present particular problems in the formulation of unit dosages containing them. In part, these problems arise from the fact that the compounds need to be dosed in relatively large amounts. This means that in order for a unit dose to be of a size which does not make it too difficult to swallow, assisting with patient compliance, the inclusion level of the active ingredient needs to be quite high, leaving very little formulation space for excipients.

There is a need for unit doses containing such inorganic solid phosphate binders which include high levels of the pharmaceutically active ingredient yet which maintain physical integrity and stability on storage. There is also a need for such unit doses to disintegrate in order to release the solid inorganic phosphate binder in the stomach and to give rapid phosphate binding, but not to disintegrate excessively in the mouth or oesophagus resulting in an unpleasant taste and potential lack of patient compliance. There is also a need for processing routes for forming the solid inorganic phosphate binders into unit doses without problems caused by poor flowability of the material and yet without excessive hindering of the rate of phosphate binding for the material.

SUMMARY OF INVENTION

Thus, a first aspect of the present invention provides a granular material comprising (i) at least 50% by weight based on the weight of the granular material of solid water-insoluble mixed metal compound capable of binding phosphate of formula (I):

$$M^{II}_{1-x}M^{III}_{x}(OH)_2 A^{n-}_{y/n} \cdot zH_2O \qquad (I)$$

where $M^{II}$ is at least one of magnesium, calcium, lanthanum and cerium; $M^{III}$ is at least iron(III); $A^{n-}$ is at least one n-valent anion; $x=\Sigma ny$; $0<x\leq 0.67$, $0<y\leq 1$, and $0\leq z\leq 10$; (ii) from 3 to 12% by weight based on the weight of the granular material of non-chemically bound water, and (iii) no greater than 47% by weight based on the weight of the granular material of excipient.

A second aspect of the invention provides a unit dose for oral administration comprising a water-resistant capsule containing granules according to the first aspect of the invention.

A third aspect of the invention provides a unit dose for oral administration comprising a compacted tablet of granules according to the first aspect of the invention. Preferably, the tablet is coated with a water-resistant coating.

The solid water-insoluble inorganic compound capable of binding phosphate is referred to herein as an "inorganic phosphate binder" or as "binder".

References herein to "granules" equally apply to the "granular material" of the present invention.

It has been found that surprisingly, for such granules for use in unit doses, the level of water is critical in maintaining the physical integrity of the granules, and of unit doses prepared from the granules during storage. Correct levels of water provide good phosphate binding when the granules are ingested, without excessive break-up of the granules or of tablets formed from the granules in the mouth. It has also been found that such granules bind phosphate rapidly.

It has also been found that by providing the compound of formula I is a granular form rather that as a powder the flowability problems of powders and the storage stability problems of powder based tablets are overcome while the advantages of such systems with regard to rapid disintegration are maintained. Fine particle size, for example as found in powders, results in very poor flowability of the powder resulting in poor tablet compression (tablets too soft and not homogenous), poor storage stability and problems with equipment loading. Surprisingly, we have found that by first increasing the particle size of the finely divided particulate by granulation of the mixture of compound of formula I with excipients, drying the granules to a controlled moisture content and reducing the granule size back down again to a more finely divided particulate (such as the 'small' particle size distribution of Table 7) we can obtain suitable phosphate binding granules without requiring substantial increased levels of excipients whilst enabling operation of tablet compression machines typically capable of commercial production rates (for example from 10,000 to 150,000 tablets/hour) and compression into a suitably shaped tablet of a compact size which is not too difficult to swallow. In contrast, typical tablet formulations such as those disclosed in U.S. Pat. No. 4,415,555 or U.S. Pat. No. 4,629,626 Miyata et al of hydrotalcite materials resulted in formulations comprising less than 50% of the active compound and/or requiring hydrothermal treatment of the hydrotalcite to increase storage stability of the tablets.

The water content of the granules of the present invention is expressed in terms of the content of non-chemically bound water in the granules. This non-chemically bound water therefore excludes chemically bound water. Chemically bound water may also be referred to as structural water.

The amount of non-chemically bound water is determined by pulverizing the granules, heating at 105° C. for 4 hours and immediately measuring the weight loss. The weight equivalent of non-chemically bound water driven off can then be calculated as a weight percentage of the granules.

It has been found that if the amount of non-chemically bound water is less than 3% by weight of the granules, tablets formed from the granules become brittle and may break very easily. If the amount of non-chemically bound water is greater than 10% by weight of the granules, disintegration time of the granules and of tablets prepared from the granules increases, with an associated reduction in phosphate binding rate and the storage stability of the tablet or granules becomes unacceptable leading to crumbling on storage.

By water-insoluble phosphate binder, it is meant that the binder has a solubility in distilled water at 25° C. of 0.5 g/liter or less, preferably 0.1 g/liter or less, more preferably 0.05 g/liter or less.

The water-resistant capsule of the second aspect of the invention is suitably a hard gelatine capsule. For the water-resistant capsule, by water-resistant it is meant that on storage for 4 weeks at 40° C. and 70% relative humidity, the water uptake of the unit dose, (i.e. the capsule containing the granules of the first aspect of the invention), due to moisture content change is preferably less than 10% more preferably less than 5% by weight of the unit dose. Such capsules have the advantage of helping stabilise the moisture content of the granules on storage The tablets of third aspect of the invention preferably have a water-resistant coating in order to inhibit moisture ingress into the tablet or moisture loss from the tablet on storage. However, the water resistant coating must allow break-up of the tablet after a suitable time following ingestion such that the inorganic solid phosphate binder can be effective in the gut of the patient. By water-resistant it is meant that on storage for 4 weeks at 40° C. and 70% relative humidity, the water uptake of the coated tablet due to moisture content change is preferably less than 10% more preferably less than 5% by weight of the coated tablet. In a preferred aspect by water-resistant it is meant that on storage for 12 months at 25° C. and 60% relative humidity, the water uptake of the coated tablet due to moisture content change is preferably less than 10% more preferably less than 5% by weight of the coated tablet. In a further preferred aspect by water-resistant it is meant that on storage for 12 months at 30° C. and 65% relative humidity, the water uptake of the coated tablet due to moisture content change is preferably less than 10% more preferably less than 5% by weight of the coated tablet. In a preferred aspect by water-resistant it is meant that on storage for 6 months at 40° C. and 75% relative humidity, the water uptake of the coated tablet due to moisture content change is preferably less than 10% more preferably less than 5% by weight of the coated tablet.

DETAILED DESCRIPTION AND PREFERRED EMBODIMENTS

Phosphate Binders

By binding of phosphate ions, it is meant that the phosphate ions are removed from solution and are immobilised in the atomic structure of the water-insoluble inorganic solid phosphate binder.

Suitable water-insoluble inorganic solids for binding phosphate ions from solution (hereinafter also called inorganic phosphate binders or as binders for brevity) are disclosed for instance in WO 99/15189 and include sulphates such as calcium sulphate, which has been alkali treated, mixtures of different metal salts and mixed metal compounds as described below. Preferred water-insoluble inorganic solids for use as phosphate binders in the tablets of the invention are mixed metal compounds.

Because of their water-insolubility, it is preferred if the inorganic phosphate binders used in the tablets of the invention are in a finely divided particulate form such that an adequate surface area is provided over which phosphate binding or immobilisation can take place. Suitably, the inorganic phosphate binder particles have a weight median particle diameter ($d_{50}$) of from 1 to 20 micrometers, preferably from 2 to 11 micrometers. Preferably, the inorganic phosphate binder particles have a $d_{90}$ (i.e. 90% by weight of the particles have a diameter less than the $d_{90}$ value) of 100 micrometers or less.

Mixed Metal Binders

The present invention provides a granular material comprising (i) at least 50% by weight based on the weight of the granular material of solid mixed metal compound capable of binding phosphate of formula (I):

$$M^{II}_{1-x}M^{III}_{x}(OH)_2A^{n-}{}_{y}\cdot zH_2O \qquad (I)$$

where $M^{II}$ is at least one of magnesium, calcium, lanthanum and cerium; $M^{III}$ is at least iron(III); $A^{n-}$ is at least one n-valent anion; $x=\Sigma ny$; $0<x\leq 0.67$, $0<y\leq 1$, and $0\leq z\leq 10$; (ii) from 3 to 12% by weight based on the weight of the granular material of non-chemically bound water, and (iii) no greater than 47% by weight based on the weight of the granular material of excipient. The present invention further provides a unit dose for oral administration comprising a water-resistant capsule containing the granular material. The present invention yet further provides a unit dose for oral administration comprising a compacted tablet of the granular material. Preferably, the tablet is coated with a water-resistant coating.

A preferred inorganic phosphate binder is solid water-insoluble mixed compound of formula (I):

$$M^{II}_{1-x}M^{III}_{x}(OH)_2A^{n-}{}_{y}\cdot zH_2O \qquad (I)$$

where $M^{II}$ is at least one bivalent metal; $M^{III}$ is at least one trivalent metal; $A^{n-}$ is at least one n-valent anion; $x=\Sigma ny$ and x, y and z fulfil $0<x\leq 0.67$, $0<y\leq 1$, $0\leq z\leq 10$.

In one preferred aspect $0.1<x$, such as $0.2<x$, $0.3<x$, $0.4<x$, or $0.5<x$. In one preferred aspect $0<x\leq 0.5$. It will be understood that $x=[M^{III}]/([M^{II}]+[M^{III}])$ where $[M^{II}]$ is the number of moles of $M^{II}$ per mole of compound of formula I and $[M^{III}]$ is the number of moles of $M^{III}$ per mole of compound of formula I.

In one preferred aspect $0<y\leq 1$. Preferably $0\leq y\leq 0.8$. Preferably $0\leq y\leq 0.6$. Preferably $0<y\leq 0.4$. Preferably $0.05<y\leq 0.3$. Preferably $0.05<y\leq 0.2$. Preferably $0.1<y\leq 0.2$. Preferably $0.15<y\leq 0.2$.

In one preferred aspect $0\leq z\leq 10$. Preferably $0\leq z\leq 8$. Preferably $0\leq z\leq 6$. Preferably $0\leq z\leq 4$. Preferably $0\leq z\leq 2$. Preferably 0.1≤z≤2. Preferably 0.5≤z≤2. Preferably 1≤z≤2. Preferably 1≤z≤1.5. Preferably 1≤z≤1.4. Preferably 1.2≤z≤1.4. Preferably z is approximately 1.4.

Preferably, 0<x≤0.5, 0<y≤1, and 0≤z≤10.

It will be appreciated that each of the preferred values of x, y and z may be combined. Thus any combination of each of the values listed in the table below are specifically disclosed herein and may be provided by the present invention.

| x | y | z |
|---|---|---|
| 0.1 < x | 0 < y ≤ 0.8 | 0 ≤ z ≤ 10 |
| 0.2 < x | 0 < y ≤ 0.6 | 0 ≤ z ≤ 8 |
| 0.3 < x | 0 < y ≤ 0.4 | 0 ≤ z ≤ 6 |
| 0.4 < x | 0.05 < y ≤ 0.3 | 0 ≤ z ≤ 4 |
| 0.5 < x | 0.05 < y ≤ 0.2 | 0 ≤ z ≤ 2 |
| 0 < x ≤ 0.67 | 0.1 < y ≤ 0.2 | 0.1 ≤ z ≤ 2 |
| 0 < x ≤ 0.5 | 0.15 < y ≤ 0.2 | 0.5 ≤ z ≤ 2 |
|  |  | 1 ≤ z ≤ 2 |
|  |  | 1 ≤ z ≤ 1.5 |
|  |  | 1 ≤ z ≤ 1.4 |
|  |  | 1.1 ≤ z ≤ 1.4 |

In the above formula (I), when A represents more than one anion, the valency (n) of each may vary. "Σny" means the sum of the number of moles of each anion multiplied by its respective valency.

In formula (I), $M^{II}$ is preferably selected from Mg (II), Zn (II), Fe (II), Cu (II), Ca (II), La (II) and Ni(II). Of these, Mg is especially preferred. $M^{III}$ is preferably selected from Mn(III), Fe(III), La(III), Ni (III) and Ce(III). Of these, Fe(III) is especially preferred. Herein, (II) means a metal in a divalent state and (III) means a metal in a trivalent state.

$A^{n-}$ is preferably selected from one or more of carbonate, hydroxycarbonate, oxo-anions (eg. nitrates, sulphate), metal-complex anion (eg. ferrocyanide), polyoxo-metalates, organic anions, halide, hydroxide and mixtures thereof. Of these, carbonate is especially preferred.

Preferably, the compound comprises less than 200 g/kg of Aluminium, more preferably less than 100 g/kg, even more preferably less than 50 g/kg expressed as weight of aluminium metal per weight of compound.

More preferably, only low levels of aluminium are present such as less than 10 g/kg, preferably less than 5 g/kg.

Even more preferably, the compound is free from aluminium (Al). By the term "free from aluminium" it is meant that the material termed "free from aluminium" comprises less than 1 g/kg, more preferably less than 500 mg/kg, even more preferably less than 200 mg/kg, most preferably less than 120 mg/kg expressed as weight of elemental aluminium per weight of compound.

Suitably the compound contains iron(III) and at least one of Magnesium, Calcium, Lanthanum or Cerium, more preferably at least one of Magnesium, Lanthanum or Cerium, most preferably Magnesium.

Preferably, the compound comprises less than 100 g/kg of calcium, more preferably less than 50 g/kg, even more preferably less than 25 g/kg expressed as weight of elemental calcium per weight of compound.

More preferably, only low levels of calcium are present such as less than 10 g/kg, preferably less than 5 g/kg.

Even more preferably, the compound is free from calcium. By the term "free from calcium" it is meant that the material termed "free from calcium" comprises less than 1 g/kg, more preferably less than 500 mg/kg, even more preferably less than 200 mg/kg, most preferably less than 120 mg/kg expressed as weight of elemental calcium per weight of material.

Preferably, the binder compound is free from calcium and free from aluminium.

The final unit dose, comprising granules and any other material making up the final unit dose, as a whole, is also preferably free from aluminium and/or preferably free from calcium, using the definitions as detailed above.

Preferably the solid mixed metal compound comprises at least some material which is a Layered Double Hydroxide (LDH). More preferably, the mixed metal compound of formula (I) is a layered double hydroxide. As used herein, the term "Layered Double Hydroxide" is used to designate synthetic or natural lamellar hydroxides with two different kinds of metallic cations in the main layers and interlayer domains containing anionic species. This wide family of compounds is sometimes also referred to as anionic clays, by comparison with the more usual cationic clays whose interlamellar domains contain cationic species. LDHs have also been reported as hydrotalcite-like compounds by reference to one of the polytypes of the corresponding [Mg—Al] based mineral.

A particularly preferred mixed metal compound contains at least one of carbonate ions, and hydroxyl ions.

A particularly preferred compound contains as $M^{II}$ and $M^{III}$, magnesium and iron (III) respectively.

The solid mixed metal compound or compounds may be suitably made by coprecipitation from a solution, e.g. as described in WO 99/15189, followed by centrifugation or filtration, then drying, milling and sieving. The mixed metal compound is then rewetted again as part of the wet-granulation process and the resulting granules dried in a fluid-bed. The degree of drying in the fluid-bed is used to establish the desired water content of the final tablet.

Alternatively, mixed metal compound may be formed by heating an intimate mixture of finely divided single metal salts at a temperature whereby solid-solid reaction can occur, leading to mixed metal compound formation.

The solid mixed metal compound of formula (I) may be calcined by heating at temperatures in excess of 200° C. in order to decrease the value of z in the formula. In this case, it may be necessary to add water after calcination and prior to incorporation of the solid mixed metal compound in the granules in order to achieve the desired non-chemically bound water content of the granules.

It will be appreciated by those skilled in the art that the water provided by $zH_2O$ in formula (I) may provide part of the 3 to 12% by weight of non-chemically bound water (based on the weight of the granular material). One skilled in the art may readily determine the value of z based on standard chemical techniques. Once the material of the present invention has been provided the amount of the non-chemically bound water may then also be readily determined in accordance with the procedure described herein.

By mixed metal compound, it is meant that the atomic structure of the compound includes the cations of at least two different metals distributed uniformly throughout its structure. The term mixed metal compound does not include mixtures of crystals of two salts, where each crystal type only includes one metal cation. Mixed metal compounds are typically the result of coprecipitation from solution of different single metal compounds in contrast to a simple solid physical mixture of 2 different single metal salts. Mixed metal compounds as used herein include compounds of the same metal type but with the metal in two different valence states e.g. Fe(II) and Fe(III) as well as compounds containing more than 2 different metal types in one compound.

The mixed metal compound may also comprise amorphous (non-crystalline) material. By the term amorphous is meant either crystalline phases which have crystallite sizes below the detection limits of x-ray diffraction techniques, or crystalline phases which have some degree of ordering, but which do not exhibit a crystalline diffraction pattern and/or true amorphous materials which exhibit short range order, but no long-range order.

The compound of formula I is preferably formed with no aging or hydrothermal treatment to avoid the crystals of the compound growing in size and to maintain a high surface area over which phosphate binding can take place. The unaged compound of formula I is also preferably maintained in a fine particle size form during the post-synthesis route to maintain good phosphate binding.

Phosphate Binding

Any reference herein to phosphate binding capacity means phosphate binding capacity as determined by the following method, unless otherwise specified. 40 mmoles/liter Sodium Phosphate solution (pH 4) is prepared and treated with the phosphate-binder. The filtered solution of the treated phosphate solution is then diluted and analysed by ICP-OES for phosphorus content.

Reagents used for this method are: Sodium Dihydrogen Phosphate Monohydrate (BDH, AnalaR™ grade), 1M hydrochloric acid, AnalaR™ water), standard phosphorous solution (10,000 µg/ml, Romil Ltd), sodium chloride (BDH).

Specific apparatus used are: Rolling hybridisation incubator or equivalent (Grant Boekal HIW7), 10 ml blood collection tubes, Reusable Nalgene screw cap tubes (30 ml/50 ml), 10 ml disposable syringes, 0.45 µm single use syringe filter, ICP-OES (inductively coupled plasma-optical emission spectrometer).

Phosphate solution is prepared by weighing 5.520 g (+/−0.001 g) of sodium dihydrogen phosphate followed by addition of some AnalaR™ water and transferring to a 1 ltr volumetric flask.

To the 1 liter volumetric flask is then added 1 M HCl drop-wise to adjust the pH to pH 4 (+/−0.1) mixing between additions. The volume is then accurately made up to one liter using AnalaR™ water and mixed thoroughly.

NaCl solution is prepared by accurately weighing out 5.85 g (+/−0.02 g) of NaCl and quantitatively transferring into a 1 liter volumetric flask after which the volume is made up with AnalaR™ water and mixed thoroughly.

Calibration Standards are prepared by pipetting into 100 ml volumetric flasks the following solutions:

| Flask No. | 1 | 2 | 3 | 4 |
|---|---|---|---|---|
| Identification | Blank | Std 1 | Std 2 | Std 3 |
| NaCl solution | 10 ml | 10 ml | 10 ml | 10 ml |
| 10000 ppm P Std | 0 ml | 4 ml (400 ppm) | 2 ml (200 ppm) | 1 ml (100 ppm) |

The solutions are then made up to volume with AnalaR™ water and thoroughly mixed. These solutions are then used as calibration standards for the ICP-OES apparatus. The phosphate binder samples are then prepared in accordance with the procedure described hereafter and measured by ICP-OES. The ICP-OES results are initially expressed as ppm but can be converted to mmol using the equation: mmol=(reading ICP-OES in ppm/molecular weight of the analyte)×4 (dilution factor).

Aliquots of each test sample, each aliquot containing 0.5 g of the phosphate binder, are placed into 30 ml screw top Nalgene tubes. If the test sample is a unit dose comprising 0.5 g of the phosphate binder, it may be used as such. All samples are prepared in duplicate. 12.5 ml aliquots of the Phosphate solution are pipetted into each of the screw top tubes containing the test samples and the screw cap fitted. The prepared tubes are then placed into the roller incubator pre heated to 37° C. and rotated at full speed for a fixed time such as 30 minutes (other times may be used as shown in the Examples). The samples are subsequently removed from the roller incubator, filtered through a 0.45 µm syringe filter, and 2.5 ml of filtrate transferred into a blood collection tube. 7.5 ml of AnalaR™ water is pipetted into each 2.5 ml aliquot, and mixed thoroughly. The solutions are then analysed on the ICP-OES.

The phosphate binding capacity is determined by:
$$\text{phosphate binding (\%)}=100-(T/S\times100)$$

where
T=Analyte value for phosphate in solution after reaction with phosphate binder.
S=Analyte value for phosphate in solution before reaction with phosphate binder.

Suitably, the water-insoluble inorganic solid phosphate binders used in the granules of the present invention provide a phosphate binding capacity for the material as measured by the above method of at least 30% after 30 minutes, preferably at least 30% after 10 minutes, more preferably at least 30% after 5 minutes. Preferably the water-insoluble inorganic solid phosphate binders used in the tablets of the present invention have a phosphate binding capacity as measured by the above method of at least 40% after 30 minutes, preferably at least 30% after 10 minutes, more preferably at least 30% after 5 minutes. Even more preferably the water-insoluble inorganic solid phosphate binders used in the tablets of the present invention have a phosphate binding capacity as measured by the above method of at least 50% after 30 minutes, preferably at least 30% after 10 minutes, more preferably at least 30% after 5 minutes.

The pH of the phosphate binding measurement may be varied by use of addition of either 1M HCl or NaOH solution. The measurement may then be used to assess the phosphate binding capacity at varying pH values.

Suitably, the water-insoluble inorganic solid phosphate binders used in the tablets of the present invention have a phosphate binding capacity at a pH from 3 to 6, preferably at a pH from 3 to 9, more preferably at a pH from 3 to 10, most preferably at a pH from 2 to 10, as measured by the above method, of at least 30% after 30 minutes, preferably at least 30% after 10 minutes, more preferably at least 30% after 5 minutes.

Preferably the water-insoluble inorganic solid phosphate binders used in the tablets of the present invention have a phosphate binding capacity at a pH from 3 to 4, preferably from 3 to 5, more preferably from 3 to 6 as measured by the above method of at least 40% after 30 minutes, preferably at least 40% after 10 minutes, more preferably at least 40% after 5 minutes.

Even more preferably the water-insoluble inorganic solid phosphate binders used in the tablets of the present invention have a phosphate binding capacity at a pH from 3 to 4, preferably from 3 to 5, more preferably from 3 to 6, as measured by the above method, of at least 50% after 30 minutes, preferably at least 50% after 10 minutes, more preferably at least 50% after 5 minutes.

It will be understood that it is desirable to have high phosphate binding capability over as broad a pH range as possible.

An alternate method of expressing phosphate binding capacity using the method described above is to express the phosphate bound by the binder as mmol of Phosphate bound per gram of binder.

Using this description for phosphate binding, suitably, the water-insoluble inorganic solid phosphate binders used in the tablets of the present invention have a phosphate binding capacity at a pH from 3 to 6, preferably at a pH from 3 to 9, more preferably at a pH from 3 to 10, most preferably at a pH from 2 to 10 as measured by the above method of at least 0.3 mmol/g after 30 minutes, preferably at least 0.3 mmol/g after 10 minutes, more preferably at least 0.3 mmol/g after 5 minutes. Preferably the water-insoluble inorganic solid phosphate binders used in the tablets of the present invention have a phosphate binding capacity at a pH from 3 to 4, preferably from 3 to 5, more preferably from 3 to 6 as measured by the above method of at least 0.4 mmol/g after 30 minutes, preferably at least 0.4 mmol/g after 10 minutes, more preferably at least 0.4 mmol/g after 5 minutes. Even more preferably the water-insoluble inorganic solid phosphate binders used in the tablets of the present invention have a phosphate binding capacity at a pH from 3 to 4, preferably from 3 to 5, more preferably from 3 to 6 as measured by the above method of at least 0.5 mmol/g after 30 minutes, preferably at least 0.5 mmol/g after 10 minutes, more preferably at least 0.5 mmol/g after 5 minutes.

Granules

The granules of the present invention comprise at least 50%, preferably at least 60%, more preferably at least 70% most preferably at least 75%, by weight inorganic phosphate binder.

The granules of the present invention comprise from 3 to 12% by weight of non-chemically bound water, preferably from 5 to 10% by weight.

The remainder of the granules comprises a pharmaceutically acceptable carrier for the phosphate binder, chiefly an excipient or blend of excipients, which provides the balance of the granules. Hence the granules may comprise no greater than 47% by weight of excipient. Preferably the granules comprise from 5 to 47% by weight of excipient, more preferably from 10 to 47% by weight of excipient, more preferably from 15 to 47% by weight of excipient.

Granule Size

Suitably, at least 95% by weight of the granules have a diameter less than 1180 micrometers as measured by sieving.

Preferably, at least 50% by weight of the granules have a diameter less than 710 micrometers as measured by sieving.

More preferably, at least 50% by weight of the granules have a diameter from 106 to 1180 micrometers, preferably from 106 to 500 micrometers.

Even more preferably, at least 70% by weight of the granules have a diameter from 106 to 1180 micrometers, preferably from 106 to 500 micrometers.

Preferably the weight median particle diameter of the granules is from 200 to 400 micrometers.

Larger granules can lead to unacceptably slow phosphate binding. Too high a proportion of granules less than 106 micrometers in diameter can lead to the problem of poor flowability of the granules. Preferably, at least 50% by weight of the granules have a diameter greater than 106 micrometers as measured by sieving, more preferably at least 80% by weight.

Granule Ingredients

Suitable excipients which may be included in the granules include conventional solid diluents such as, for example, lactose, starch or talcum, as well as materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

The term excipient herein also includes auxiliary components such as tablet structurants or adhesives, disintegrants or swelling agents.

Suitable structurants for tablets include acacia, alginic acid, carboxymethylcellulose, hydroxyethylcellulose, hydroxypropylcellulose, dextrin, ethylcellulose, gelatin, glucose, guar gum, hydroxypropylmethylcellulose, kaltodextrin, methylcellulose, polyethylene oxide, povidone, sodium alginate and hydrogenated vegetable oils.

Suitable disintegrants include cross-linked disintegrants. For example, suitable disintegrants include cross-linked sodium carboxymethylcellulose, cross-linked hydroxypropylcellulose, high molecular weight hydroxypropylcellulose, carboxymethylamide, potassium methacrylatedivinyl-benzene copolymer, polymethylmethacrylate, cross-linked polyvinylpyrrolidone (PVP) and high molecular weight polyvinylalcohols.

Cross-linked polyvinylpyrrolidone (also known as crospovidone, for example available as Kollidon CL-M™ ex BASF) is an especially preferred excipient for use in the tablets of the invention. Suitably, the granules of the tablets of the invention comprise from 1 to 15% by weight of cross-linked polyvinylpyrrolidone, preferably from 1 to 10%, more preferably from 2 to 8%. Preferably, the cross-linked polyvinylpyrrolidone has a $d_{50}$ weight median particle size, prior to granulation of less than 50 micrometers (i.e. so-called B-type cross-linked PVP). Such material is also known as micronised crospovidone. It has been found that the cross-linked polyvinylpyrrolidone at these levels leads to good disintegration of the tablet but with less inhibition of phosphate binding of the inorganic phosphate binder as compared to some other excipients. The preferred sizes for the cross-linked polyvinylpyrollidone give reduced grittiness and hardness of the particles formed as the tablets disintegrate.

Another preferred excipient for use in the granules of the tablets of the invention is pregelatinised starch (also known as pregelled starch). Preferably, the granules comprise from 5 to 20% by weight of pregelled starch, more preferably 10 to 20%, even more preferably from 12 to 18% by weight. The pregelatinised starch at these levels improves the durability and cohesion of the tablets without impeding the disintegration or phosphate binding of the tablets in use. The pregelatinised starch is suitably fully pregelatinised, with a moisture content from 1 to 15% by weight and a weight median particle diameter from 100 to 250 micrometers. A suitable material is Lycotab™—a fully pregelatinised maize starch available from Roquette.

A combined excipient including both pregelatinised starch and crospovidone is particularly preferred, as this combination of excipients gives the ability to reliably form compacted tablets of various shapes, good granule homogeneity and good disintegration characteristics from the granules of the invention.

The granules may also comprise preservatives, wetting agents, antioxidants, surfactants, effervescent agents, colouring agents, flavouring agents, pH modifiers, sweeteners or taste-masking agents. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include sodium hydrogencarbonate (i.e. bicarbonate), citric acid, tartaric acid, hydrochloric acid and maleic acid. Suitable sweeteners include aspartame, acesulfame K and thaumatin. Suitable taste-masking agents include sodium hydrogencarbonate, ion-exchange resins, cyclodextrin inclusion compounds and adsorbates. Suitable wetting agents include sodium lauryl sulphate and sodium docusate. A suitable effervescent agent or gas producer is a mixture of sodium bicarbonate and citric acid.

Granulation

Granulation may be performed by a process comprising the steps of:
i) mixing the solid water-insoluble inorganic compound capable of binding phosphate with one or more excipients to produce a homogeneous mix,
ii) contacting a suitable liquid with the homogeneous mix and mixing in a granulator to form wet granules,
iii) optionally passing the wet granules though a screen to remove granules larger than the screen size,
iv) drying the wet granules to provide dry granules.
v) milling and/or sieving the dry granules.

Suitably the granulation is by wet granulation, comprising the steps of;
i) mixing the inorganic solid phosphate binder with suitable excipients to produce a homogeneous mix,
ii) adding a suitable liquid to the homogeneous mix and mixing in a granulator to form granules,
iii) optionally passing the wet granules though a screen to remove granules larger than the screen size,
iv) drying the granules.
v) milling and sieving the granules Suitable liquids for granulation include water, ethanol and mixtures thereof. Water is a preferred granulation liquid.

The granules are dried to the desired moisture levels as described hereinbefore prior to their use in tablet formation or incorporation into a capsule for use as a unit dose.

Lubricant

Prior to tabletting the granules into a unit dose composition, it is preferred that the granules are blended with a lubricant or glidant such that there is lubricant or glidant distributed over and between the granules during the compaction of the granules to form tablets.

Typically the optimum amount of lubricant required depends on the lubricant particle size and on the available surface area of the granules. Suitable lubricants include silica, talc, stearic acid, calcium or magnesium stearate and sodium stearyl fumarate and mixtures thereof. Lubricants are added to the granules in a finely divided form, typically no particles greater than 40 micrometers in diameter (ensured typically by sieving). The lubricant is suitably added to the granules at a level of from 0.1 to 0.4%, preferably from 0.2 to 0.3% by weight of the granules. Lower levels can lead to sticking or jamming of the tablet die whereas higher levels may reduce the rate of phosphate binding or hinder tablet disintegration. Salts of fatty acids may be used as lubricants, such as calcium and/or magnesium stearate. A preferred lubricant is selected from the group consisting of magnesium stearate, sodium stearyl fumarate and mixtures thereof. It has been found that some lubricants, such as fatty acids, lead to pitting and loss of integrity in the coating layer of the tablets. It is thought that this may arise from partial melting of the lubricant as the coating layer is dried. Hence it is preferred that the lubricant has a melting point in excess of 55° C.

Tablets

The tablets of the third aspect of invention may be prepared by compressing granules, under high pressure, in order to form a tablet having the necessary crushing strength for the handling required during packaging and distribution. The use of granules formed from a granulated powder mixture improves flowability from storage hoppers to the tabletting press which in turn benefits the efficiency of tablet processing. The inorganic phosphate binders used in the tablets of the present invention typically have poor flowability properties at their desired particle size as detailed hereinbefore. Because it is desired that the tablets of the invention comprise high levels of inorganic phosphate binder, of the order of 50% or more by weight of the tablet, the inorganic phosphate binder must be formed into granules prior to tablet formation. A fine powder is apt to pack or "bridge" in the hopper, feed shoe or die, and thus tablets of even weight or even compression are not easily obtainable. Even if it were possible to compress fine powders to a satisfactory degree, air may be trapped and compressed, which may lead to splitting of the tablet on ejection. The use of granules helps to overcome these problems. Another benefit of granulation is the increase in bulk density of the final tablet when prepared from granules rather than from fine powder, reducing the size of the final tablet and improving the likelihood of patient compliance.

The tablets of the invention may be circular but are preferably generally bolus- or torpedo-shaped (also known as double convex oblong shaped tablet,) i.e. having an elongate dimension, in order to assist swallowing of larger doses. It may for example be in the form of a cylinder with rounded ends or elliptical in one dimension and circular in an orthogonal dimension, or elliptical in both. Some flattening of one or more parts of the overall shape is also possible.

Where the tablet is in the form of a tablet provided with a "belly-band", it is preferred if the width of the belly-band is 2 mm or more. It has been found that smaller belly-bands can lead to insufficient coverage or chipping or loss of integrity of the water-resistant coating of the tablet.

The tablets of the second aspect of the invention preferably have a hardness from 5 to 30 kgf as measured using a Holland C50 tablet hardness tester.

Water Resistant Coating

The tablets of the second aspect of the invention, once formed from the granules of the first aspect of the invention, are preferably provided with a water-resistant coating.

The water-resistant coating may be applied to the tablet by any of the usual pharmaceutical coating processes and equipment. For example, tablets may be coated by fluid bed equipment (for example a "Wurster" type fluid bed dryer) coating pans (rotating, side vented, convention etc), with spray nozzles or guns or other sprayer types or by dipping and more recent techniques including Supercell tablet coater from Niro PharmaSystems. Variations in available equipment include size, shape, location of nozzles and air inlets and outlets, air flow patterns and degree of instrumentation. Heated air may be used to dry the sprayed tablets in a way that allows continuous spraying while the tablets are being simultaneously dried. Discontinuous or intermittent spraying may also be used, but generally requires longer coating cycles. The number and position of nozzles may be varied, as needed depending on the coating operation and the nozzles(s) is preferably aimed perpendicularly or nearly perpendicular to the bed although other direction(s) of aim may be employed if desired. A pan may be rotated at a speed selected from a plurality of operating speeds. Any suitable system capable of applying a coating composition to a tablet may be used. Virtually any tablet is acceptable herein as a tablet to be coated. The term "tablet" could include tablet, pellet or pill. Typically the preferred tablet will be in a form sufficiently stable physically and chemically to be effectively coated in a system which involves some movement of a tablet, as for example in a fluidized bed, such as in a fluidized bed dryer or a side vented coating pan, combinations thereof and the like. Tablets may be coated directly, i.e. without a subcoat to prepare the surface. Subcoats or topcoats may of course be used. If desired, the same or a similar coating application system can be employed for both a first or second or more coating applications. The coating composition is prepared according to the physical properties of its constituents, i.e. soluble materials are dissolved, insoluble materials are dispersed. The type of mixing used is also based on the properties of the ingredients. Low shear liquid mixing is used for soluble materials and high shear liquid mixing is used for insoluble materials. Usually the coating formulation consists of two parts, the colloidal polymer suspension and the pigment suspension or solution (eg red oxide or Quinoline yellow dye). These are prepared separately and mixed before use.

A wide range of coating materials may be used, for example, cellulose derivatives, polyvinylpyrrolidone, polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of methacrylate and tertiary amino alkyl methacrylate, copolymers of ethylacrylate methyl methacrylate and quaternary amino alkyl methacrylate and combinations of two or more hereof. Preferably, salts of methacrylate copolymers are used, eg. butylated methacrylate copolymer (commercially available as Eudragit EPO).

The coating is suitably present as 0.05 to 10% by weight of the coated tablet, preferably from 0.5% to 7%. Preferably the coating material is used in combination with red iron oxide pigment ($Fe_2O_3$) (1% or more, preferably 2% or more by weight of the dried coating layer) which is dispersed throughout the coating material and provides an even colouring of the coating layer on the tablet giving a pleasant uniform appearance.

In addition to protecting the tablet core from moisture loss or ingress on storage, the water resistant coating layer also helps to prevent the rapid breakup of the tablet in the mouth, delaying this until the tablet reaches the stomach. With this purpose in mind, it is preferred if the coating material has low solubility in alkaline solution such as found in the mouth, but more soluble in neutral or acid solution. Preferred coating polymers are salts of methacrylate copolymers, particularly butylated methacrylate copolymer (commercially available as Eudragit EPO). Preferably the coating layer comprises at least 30% by weight of a coating polymer, more preferably at least 40% by weight.

The water loss or uptake of coated tablets is suitably measured as detailed hereinbefore for the measurement of the non-chemically bound water content for granules. From a set of freshly prepared coated tablets, some are measured for non-chemically bound water immediately following preparation, and others are measured after storage as detailed above.

In another aspect, the invention provides a method for preparing a tablet according to the first aspect of the invention, the method comprising granulating a water-insoluble inorganic solid phosphate binder with a pharmaceutically acceptable excipient and optionally, any other ingredients, forming a tablet from the granules by compression and optionally applying a water-resistant coating to the tablet so formed.

Capsules

Suitable capsules for use in the second aspect of the invention are hard gelatine capsules, although other suitable capsule films may be used.

Use of Unit Doses

For treatment of and prophylaxis of hyperphosphataemia, amounts of from 0.1 to 500, preferably from 1 to 200, mg/kg body weight of inorganic phosphate binder are preferably administered daily to obtain the desired results. Nevertheless, it may be necessary from time to time to depart from the amounts mentioned above, depending on the body weight of the patient, the animal species of the patient and its individual reaction to the drug or the kind of formulation or the time or interval in which the drug is applied. In special cases, it may be sufficient to use less than the minimum amount given above, whilst in other cases the maximum dose may have to be exceeded. For a larger dose, it may be advisable to divide the dose into several smaller single doses. Ultimately, the dose will depend upon the discretion of the attendant physician. Administration before meals, e.g. within one hour before a meal is suitable. Alternatively, the dose may be taken with a meal.

A typical tablet of the invention for human adult administration may comprise from 1 mg to 5 g, preferably from 10 mg to 2 g, more preferably from 100 mg to 1 g, such as from 150 mg to 750 mg, from 200 mg to 750 mg or from 250 mg to 750 mg of water-insoluble inorganic solid phosphate binder.

Preferably the unit doses of the invention comprise at least 200 mg of a water-insoluble solid inorganic phosphate binder. Preferably the unit doses of the invention comprise at least 250 mg of a water-insoluble solid inorganic phosphate binder Preferably the unit doses of the invention comprise at least 300 mg of a water-insoluble solid inorganic phosphate binder. A more preferred unit dose comprises 500 mg of the phosphate binder. The preferred unit dose weight is less than 750 mg, more preferably less than 700 mg, to aid with patient compliance for oral dosage. A particularly preferred unit dose contains 200 mg (±20 mg) of a water-insoluble solid inorganic phosphate binder. A particularly preferred unit dose contains 250 mg (±20 mg) of a water-insoluble solid inorganic phosphate binder. A particularly preferred unit dose contains 300 mg (±20 mg) of a water-insoluble solid inorganic phosphate binder. When the unit dose is a tablet, the preferred unit dose weight includes any optional coating.

The tablet forms may be packaged together in a container or presented in foil strips, blister packs or the like, e.g. marked with days of the week against respective doses, for patient guidance.

In the further aspects of the invention detailed below, granular material refers to the granules of the first aspect of the invention.

An aspect of the invention is the granular material for use in or as a medicine on humans or animals, particularly as a medicine for the binding of phosphate, more particularly for the treatment of hyperphosphataemia.

Another aspect is the use of the granular material in the manufacture of a medicament for use on animals or humans in the treatment or therapy of a condition or disease associated with adverse phosphate levels, particularly elevated plasma phosphate levels, particularly hyperphosphataemia.

Another aspect is a method for the treatment or therapy of a condition or disease associated with adverse phosphate levels, particularly elevated plasma phosphate levels, particularly hyperphosphataemia by oral administration of the granular material to humans or animals.

Storage

As discussed herein, we have found that the system of the present invention can provide tablets which are stable of over a period of at least 12 months (see Table7 for particle size of small and large granules) determined at 25 C/60RH and 30 C/65RH. Under more extreme storage conditions (40 C/75RH) the storage stability is at least 6 months for both granule types.

Further Aspects

Further aspects of the present invention are described in the following numbered paragraphs:

1. Granules comprising at least 50% by weight of water-insoluble inorganic solid phosphate binder, from 3 to 12% by weight of non-chemically bound water and up to 47% by weight of excipient.
2. Granules according to paragraph 1 wherein the water-insoluble inorganic solid phosphate binder is a mixed metal compound.
3. Granules according to paragraph 2, wherein the mixed metal compound is a compound of formula (I):

$$M^{II}_{1-x}M^{III}_{x}(OH)_2A^{n-}_{y}.zH_2O \qquad (I)$$

where $M^{II}$ is at least one bivalent metal; $M^{III}$ is at least one trivalent metal; $A^{n-}$ is at least one n-valent anion; $x=\Sigma ny$ and x, y and z fulfil $0<x\leq0.67$, $0<y\leq1$, $0\leq z\leq10$.
4. Granules according to paragraph 3 wherein $x=\Sigma ny$ and x, y and z fulfil $0<x\leq0.5$, $0<y\leq1$, $0\leq z\leq10$.
5. Granules according to any one of paragraphs 2 to 4 wherein the mixed metal compound is free from Aluminium and contains the metals iron(III) and at least one of Magnesium, Calcium, Lanthanum or Cerium.
6. Granules according to any one of paragraphs 3 to 5 wherein the mixed metal compound of formula (I) is a layered double hydroxide.
7. Granules according to any one of paragraphs 3 to 6 wherein the mixed metal compound contains at least one of hydroxyl and carbonate ions and contains as the metals iron (Ill) and magnesium.
8. Granules according to any one of paragraphs 1 to 7, wherein the granules comprise from 5 to 15% by weight of polyvinyl pyrrolidone as an excipient.
9. Granules according to any one of paragraphs 1 to 8, comprising from 10 to 20% by weight of pregelatinised starch as an excipient.
10. Granules according to any one of paragraphs 1 to 9 wherein the granules have a diameter less than 1000 micrometers.
11. A unit dose for oral administration comprising a water resistant capsule containing granules according to any preceding paragraph.

12. A unit dose for oral administration comprising a compacted tablet of granules according to any of paragraphs 1 to 10.
13. A unit dose according to paragraph 12 further comprising a lubricant between the granules.
14. A unit dose according to paragraph 13 comprising magnesium stearate as lubricant between the granules.
15. A unit dose according to any one of paragraphs 12 to 14 coated with a water-resistant coating.
16. A unit dose according to paragraph 15 wherein the water-resistant coating comprises at least 30% by weight of a butylated methacrylate copolymer.
17. A unit dose according to any one of paragraphs 12 to 16 wherein the tablet is provided with a belly band having a width of 2 mm or more.
18. A unit dose according to any one of paragraphs 11 to 17 comprising at least 300 mg of a water-insoluble inorganic solid phosphate binder.
1A. A granular material comprising
(i) at least 50% by weight based on the weight of the granular material of solid water-insoluble inorganic compound capable of binding phosphate,
(ii) from 3 to 12% by weight based on the weight of the granular material of non-chemically bound water, and
(iii) no greater than 47% by weight based on the weight of the granular material of excipient.
2A. A granular material according to paragraph 1A wherein the water-insoluble inorganic solid phosphate binder is a mixed metal compound.
3A. A granular material according to paragraph 2A, wherein the mixed metal compound is a compound of formula (I):

$$M^{II}_{1-x}M^{III}_{x}(OH)_2A^{n-}_{y}.zH_2O \qquad (I)$$

where $M^{II}$ is at least one bivalent metal; $M^{III}$ is at least one trivalent metal; $A^{n-}$ is at least one n-valent anion; $x=\Sigma ny$; $0<x\leq0.67$, $0<y\leq1$, and $0\leq z\leq10$.
4A. A granular material according to paragraph 3A wherein $x=\Sigma ny$; $0<x\leq0.5$, $0<y\leq1$, and $0\leq z\leq10$.
5A. A granular material according to paragraph 3A or 4A wherein the mixed metal compound of formula (I) is a layered double hydroxide.
6A. A granular material according to any one of paragraphs 2A to 5A wherein the mixed metal compound contains at least one of hydroxyl and carbonate ions and contains as the metals iron (Ill) and magnesium.
7A. A granular material according to any one of paragraphs 1A to 6A wherein the water-insoluble inorganic compound is free from Aluminium.
8A. A granular material according to any one of paragraphs 1A to 7A wherein the water-insoluble inorganic compound contains iron(III) and at least one of Magnesium, Calcium, Lanthanum or Cerium.
9A. A granular material according to any one of paragraphs 1A to 8A, wherein the granular material comprises from 5 to 20% by weight of pregelatinised starch as excipient based on the weight of the granular material.
10A. A granular material according to any one of paragraphs 1 to 9A, comprising from 1 to 15% by weight of polyvinyl pyrrolidone as excipient based on the weight of the granular material.
11A. A granular material according to any one of paragraphs 1A to 10A wherein at least 95% by weight of the granules of the granular material have a diameter less than 1180 micrometers.
12A. A unit dose for oral administration comprising a water resistant capsule containing a granular material according to any one of paragraphs 1A to 11A.

13A. A unit dose for oral administration comprising a compacted tablet of a granular material according to any of paragraphs 1A to 11A.
14A. A unit dose according to paragraph 13A further comprising a lubricant between the granules.
15A. A unit dose according to paragraph 14A wherein the lubricant is or comprises magnesium stearate.
16A. A unit dose according to any one of paragraphs 13A to 15A coated with a water-resistant coating.
17A. A unit dose according to paragraph 16A wherein the water-resistant coating comprises at least 30% by weight of a butylated methacrylate copolymer.
18A. A unit dose according to any one of paragraphs 16A to 17A wherein the tablet has a belly band having a width of 2 mm or more.
19A. A unit dose according to any one of paragraphs 12A to 18A wherein the solid water-insoluble inorganic compound capable of binding phosphate is present in an amount of at least 300 mg.
20A. A process for the preparation of a granular material as defined in any one of paragraphs 1A to 11A comprising the steps of:
i) mixing the solid water-insoluble inorganic compound capable of binding phosphate with one or more excipients to produce a homogeneous mix,
ii) contacting a suitable liquid with the homogeneous mix and mixing in a granulator to form wet granules,
iii) optionally passing the wet granules though a screen to remove granules larger than the screen size,
iv) drying the wet granules to provide dry granules.
v) milling and/or sieving the dry granules.
21A. A process according to paragraph 20A where in the liquid is selected from water, ethanol and mixtures thereof.
22A. A granular material according to any one of paragraphs 1A to 11A for use in medicine.
23A. Use of a granular material according to any one of paragraphs 1A to 11A in the manufacture of a medicament for binding of phosphate.
24A. Use of a granular material according to any one of paragraphs 1A to 11A in the manufacture of a medicament for use in the therapy of a condition or disease associated with phosphate levels.
25A. Use of a granular material according to any one of paragraphs 1A to 11A in the manufacture of a medicament for use in the therapy of a condition or disease associated with adverse phosphate levels.
26A. Use of a granular material according to any one of paragraphs 1A to 11A in the manufacture of a medicament for use in the therapy of a condition or disease associated with elevated plasma phosphate levels.
27A. Use of a granular material according to any one of paragraphs 1A to 11A in the manufacture of a medicament for use in the therapy of hyperphosphataemia.

The present invention will now be explained in more detail by way of the following non-limiting examples.

EXAMPLES

The phosphate binder used in the examples below was formed by the reaction of aqueous solutions of magnesium sulphate and ferric sulphate in the presence of sodium hydroxide and sodium carbonate. The synthesis reaction is described by: $4MgSO_4 + Fe_2(SO_4)_3 + 12\ NaOH + Na_2CO_3 \rightarrow Mg_4Fe_2(OH)_{12}.CO_3.nH_2O + 7Na_2SO_4$. The precipitation was carried out at approximately pH 10.3 at ambient temperature (15-25° C.). The resulting precipitate was filtered, washed, dried, milled and then sieved such that all material is less than 106 micron. The formula of the phosphate binder was: $Mg_4Fe_2(OH)_{12}.CO_3.nH_2O$ and had the following XRF composition: MgO=29.0%, $Fe_2O_3$=28.7%, Mg:Fe mole ratio=2:1. The XRF values take into account all water present in the phosphate binder. XRD showed that the phosphate binder was characterised by the presence of the poorly crystalline hydrotalcite type structure.

TABLE 1

| Material | Example | | | | | | |
|---|---|---|---|---|---|---|---|
| | 1 | 2 | 3 | 4 | 5 | 6 | 7 |
| Granules | | | | | | | |
| Phosphate Binder | 75.1 | 65.0 | 66.1 | 56.3 | 74.9 | 75.1 | 74.9 |
| Pre-gelled Starch | 14.1 | 14.0 | | | 9.4 | 14.1 | 9.4 |
| Microcrystalline Cellulose | | | 28.5 | 37.7 | | | |
| Micronised Crospovidone | 4.7 | 14.0 | | | 9.4 | 4.7 | 9.4 |
| Water content (dried granules) | 5.8 | 6.7 | 5.1 | 5.7 | 6.0 | 5.8 | 6.0 |
| Lubricants used for tabletting | | | | | | | |
| Stearic acid | 0.3 | 0.3 | 0.3 | 0.3 | 0.3 | | |
| Magnesium Stearate | | | | | | 0.3 | 0.3 |

All values in the tables are percentages by weight.

Granules were prepared using the formulations as detailed in Table 1. The dry blends were made in 125 ml batches by mixing the components in the Turbula powder blender for 5 minutes prior to granulation. The 125 gram batches of dry powder blend were granulated by the steady addition of purified water in a planar mixer until small, distinct granules were produced. Each of the powder blends required different amounts of water to granulate. Typical values of water used for granulation as weight percentage of dry powder weight are: example (1) —106%, example (2) —111%, example (3) —78%, example (4) —83%, example (5) —100%, example (6) —70-106%, example (7) —78%. Batches of granules made for each of the formulations were then combined and dried in a fluid bed drier at an air inlet temperature of 40° C. to a target moisture content of 4-6% w/w before being passed through a 1.18 mm aperture mesh to remove large granules.

The amount of water required to granulate varied dependent on phosphate binder moisture content, particle size distribution, feed-rate and degree of dispersion (water droplet size). Typically if water was used at less than 50% finer granules were obtained whereas excessive amounts of water (above 110%) resulted in lump formation. The preferred water amount was between 70 and 100%.

Tablets were made with hardnesses from 13 to 29 kgF as measured by a Holland C50 tablet hardness tester. Varying compaction pressures were used to give tablets of differing tablet hardness (as measured in Kg Force) as detailed in Table 2, from formulations 1 to 4. 0.3% stearic acid was used as a lubricant.

The disintegration time for the tablets was measured using a disintegration bath—Copley DTG 2000 IS.

The phosphate binding capacity in Table 2 was measured as detailed in the phosphate binding test described hereinbefore at pH=4 and time=30 minutes.

Friability was measured by tablet friability tester Erweka TA10

Results are shown in Table 2 for uncoated tablets prepared from granules of formulae 1, 2, 3 and 4 at three differing crush strengths (tablet hardness) (a, b and c) as indicated in the table.

TABLE 2

| Example | Disintegration Time (sec) | P (%) Binding | Tablet Hardness (KgF) | Friability (%) |
|---|---|---|---|---|
| 1a | 25 | 61 | 13 | 0 |
| 1b | 25 | 66 | 21 | 0 |
| 1c | 50 | 64 | 25 | 0 |
| 2a | 20 | 58 | 13 | 0 |
| 2b | 40 | 60 | 21 | 0 |
| 2c | 53 | 61 | 27 | 0 |
| 3a | 15 | 65 | 16 | 0 |
| 3b | 12 | 60 | 19 | 0 |
| 3c | 15 | 61 | 29 | 0 |
| 4a | 8 | 55 | 16 | 0 |
| 4b | 12 | 57 | 21 | 0 |
| 4c | 20 | 60 | 28 | 0 |

Table 3 shows the effect of the addition of a water-resistant coating comprising Eudragit EPO on tablets prepared from granules of the formulation of example 1.

The coating formulation is:

84.02% Purified water, 0.81% Sodium Dodecyl Sulphate, 8.08% Butylated methacrylate Copolymer (Eudragit EPO), 1.21% Stearic acid, 2.09% Talc, 2.83% MgStearate, 0.64% Titanium dioxide, 0.32% Red iron oxide. The coating was dried after application using hot air at 48° C.

Coating levels disclosed herein are determined from the increase in tablet weight before and after application of the coating formulation and drying in hot-air at 48° C.

TABLE 3

| Coating Level (% weight of coated tablet) | Disintegration Time (s) |
|---|---|
| 0.69 | 45 |
| 2.34 | 45-59 |
| 2.83 | 51-63 |
| 4.39 | 80-140 |

From Table 3 it can be seen that a coating has the effect of delaying the disintegration of the tablets.

Table 4 shows the effect of different coating type and lubricants on the storage behaviour and tablet characteristics for tablets formed with a hardness of 10 to 15 kgF from the granules of examples 1, 5, 6 and 7. Tablets from examples 1 and 5 included 0.3% by weight stearic acid as lubricant. Tablets from examples 6 and 7 included 0.3% by weight of Magnesium Stearate as lubricant.

TABLE 4

| Example | Disintegration Time(s) initial | Disintegration Time(s) 4 weeks | Moisture content (%) (coated tablet) Initial | Moisture content (%) (coated tablet) 4 weeks | Appearance (Visible Pitting) initial | Appearance (Visible Pitting) 4 weeks |
|---|---|---|---|---|---|---|
| Ex1 Eudragit | 158 | 226 | 8.6 | 12.7 | No | Yes |
| Ex 6 Eudragit | 422 | 128 | 8.8 | 11.3 | No | No |
| Ex 6 Opadry-AMB | 107 | 49 | 8.5 | 10.8 | No | Yes |
| Ex 5 Eudragit | 139 | 14 | 7.7 | 11.5 | No | Yes |
| Ex 7 Eudragit | 122 | 62 | 9.6 | 11.9 | No | No |
| Ex 7 Opadry-AMB | 72 | 27 | 8.5 | 11.1 | No | Yes |

The Eudragit coating is as described above

The Opadry AMB coating has Opaglos 2 Sodium Carboxymethylcellulose replacing Eudragit EPO as coating polymer with other coating ingredients as for the Eudragit coating composition.

Note that the moisture content in Table 4 is that for the complete coated tablet and not for the granules.

Storage was carried out with the tablets openly exposed at 75° C. and 40% relative humidity for 4 weeks.

From Table 4 it can be seen that the Opadry coating does not prevent pitting on storage with Mg Stearate lubricant, whereas the Eudragit does. Even the Eudragit does not prevent pitting with Stearic acid. Hence the optimal system is Mg Stearate lubricant with Eudragit Coating.

Table 5 shows the effect of granule size and moisture content on the tablet disintegration time of an uncoated tablet in water at pH 7 and in 0.1 Normal HCl both at 37° C. The formulation was as for example 6 (but with varying levels of moisture) The tablets were compacted to the same approximate hardness of 10-15 Kgf.

TABLE 5

| Granule moisture(%) | Granule diameter (μm) | Disintegration Time (s) Water | Disintegration Time(s) 0.1N HCl | Comments |
|---|---|---|---|---|
| 1.19 | <425 | 16 | 20 | Static charge dusty |
| 1.19 | <1180 | 34 | 41 | Static charge dusty |
| 7.01 | <425 | 20 | 24 | Good |
| 7.01 | <1180 | 46 | 51 | Good |
| 18.84 | <425 | 1090 | 1214 | Irregular tablet surface |
| 18.84 | <1180 | 784 | 976 | Irregular tablet surface |

The irregular tablet surface for the high moisture granules was due to excess material squeezing past the sides of the tablet die during compaction.

All granules were sieved such that less than 25% by weight of the granules had a diameter less than 106 micrometers by sieving.

From Table 5 it can be seen that increasing the granule size slows disintegration at granule moisture levels of 1.19 and 7.01%, and that the moisture content has a marked effect on both disintegration time and tablet quality.

A similar effect was found for the effect of granule size on the retardation of phosphate binding. Tablets formed from granules according to example 6 having a diameter less than 1180 μm were compared for phosphate binding as a function of time against tablets formed from granules having a diameter less than 425 μm. The tablets were both compacted to a strength of 13 kg tablet hardness and were coated with 4.5% of dried Eudragit EPO water resistant coating. The tablets prepared from the smaller granules reached 80% of the equilibrium phosphate binding after 10 minutes, whereas the tablets prepared from the larger granules took 30 minutes. The equilibrium phosphate binding is as measured after 120 minutes. The phosphate binding results were obtained according to the modified method as described hereafter.

Table 6 shows phosphate binding of coated tablets formed from granules according to Example 6 coated with Eudragit EPO in an amount of 4.5 wt % based on the coated tablet, the granules having a diameter less than 425 micrometers.

Table 6, 7 and 8 show phosphate binding (expressed as mmol of phosphate bound per gram of solid inorganic phosphate binder) at various pH values for the solution in which binding was measured.

The results of Table 6, 7, and 8 were obtained by means of the phosphate binding method described hereinbefore, but with the following modifications: 1 tablet containing 0.5 g of the phosphate binder was dispersed in 125 ml of 4 mmol/liter phosphate solution (as opposed to 12.5 ml of 40 mmol/liter). The samples were then incubated in stoppered polypropylene conical flasks in a shaking water bath at 37° C. and 200 rpm for varying times. pH of the phosphate solution was varied using 1M NaOH or HCl solution. The calibration standards for the ICP-OEC were changed accordingly to take account of the lower phosphate concentration.

TABLE 6

| | phosphate binding (mmol/g) at different times (minutes) Time | | | |
|---|---|---|---|---|
| pH | 10 | 30 | 60 | 120 |
| 3 | 0.44 | 0.54 | 0.56 | 0.59 |
| 4 | 0.44 | 0.5 | 0.53 | 0.55 |
| 9 | 0.25 | 0.33 | 0.35 | 0.38 |

Table 7 shows the effect of particle size distribution for the granules on various parameters. "Transport" refers to the ease of transfer from a hopper to the tablet press in relation to jamming and bridging. The granules were formed according to example 6. The fine granules (A) were poor.

Phosphate binding was measured by means of the phosphate binding method described previously as for Table 6 at a pH of 4.

The Phosphate binding results for A, B, C and D were from tablets (uncoated) whereas the results for E were from the granules themselves.

TABLE 7

| | fine A | small B | large C | large D | medium E |
|---|---|---|---|---|---|
| particle size by sieving (micrometers) | | | | | |
| 0 | 100 | 100 | 100 | 100 | 100 |
| 53 | 32 | 94 | 98 | 92 | 96 |
| 106 | 25 | 83 | 96 | 87 | 91 |
| 250 | 9 | 49 | 90 | | 76 |
| 500 | 3 | 0 | 71 | 51 | 47 |
| 710 | 1 | 0 | 46 | | 17 |
| 1180 | 0 | 0 | 5 | 3 | 0 |
| Transport | poor | good | good | good | good |
| Phosphate binding (minutes) | | | | | |
| 10 | 0.52 | 0.42 | 0.33 | 0.3 | |
| 20 | | 0.47 | 0.40 | | |
| 30 | 0.54 | 0.50 | 0.44 | | 0.42 |
| 46 | | 0.51 | 0.47 | 0.4 | |
| 60 | 0.54 | 0.54 | 0.48 | 0.45 | 0.49 |
| 120 | 0.57 | 0.56 | 0.51 | 0.47 | |

Examples 1-7 in uncoated tablet form, and prepared from granules having a diameter less than 1180 micrometers, were also measured using the modified phosphate binding test as shown in Table 8 at pH=4 and time=30 minutes.

TABLE 8

| Example 1 mmol PO4/g | Example 2 | Example 3 | Example 6 | Example 7 |
|---|---|---|---|---|
| 0.45 | 0.55 | 0.27 | 0.44 | 0.60 |

From Table 8 and comparison of example 2 with 3 it can be seen that example 3 has lower phosphate binding demonstrating the effect of hindering of phosphate binding by the presence of the microcrystalline cellulose and the advantage of using the preferred combination of pre-gelled starch and micronised crospovidone. This preferred combination of excipients maintained good phosphate binding as well as aiding the granulation process and showing good dispersion of the granules and tablets in water.

Material from coated tablets (containing 0.5 g of binder) formed from granules according to example 6 having diameters less than 425 micrometers was found to have the following Langmuir constants: K1 (1/mmol)=0.25 and K2 (mmol/g)=1.88.

Material from coated tablets (containing 0.5 g of binder) formed from granules according to example 6 having diameters less than 1000 micrometers was found to have the following Langmuir constants: K1 (1/mmol)=0.19 and K2 (mmol/g)=1.88.

K1 is the affinity constant and is an indication of the strength of phosphate binding while K2 is the capacity constant and is the maximum amount of phosphate that can be bound per unit weight of binder.

These Langmuir constants were determined by changing the phosphate concentration from 1 to 40 mmol/l and were calculated by performing linear regression on a plot of the unbound/bound phosphate versus the unbound phosphate measured at equilibrium. The initial pH of the phosphate solutions was pH=4, temp=37 Celsius and the selected equilibrium point was at a time t=120 minutes.

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:

1. A dried granular material comprising granules, each granule comprising a mixture of
   (i) at least 50% by weight based on the weight of the granule of solid water-insoluble inorganic mixed metal compound capable of binding phosphate and which contains iron (III) and at least one of magnesium, calcium, lanthanum or cerium, wherein the mixed metal compound is not hydrothermally treated,
   (ii) an excipient, present in an amount no greater than 47% by weight based on the weight of the granule,
   wherein at least 50% by weight of the granules of the granular material have a diameter of from 106 micrometers to 1180 micrometers.

2. The dried granular material of claim 1 wherein the mixed metal compound comprises a layered double hydroxide.

3. The dried granular material of claim 1, wherein the mixed metal compound is of formula (I):

$$M^{II}_{1-x}M^{III}_{x}(OH)_2A^{n-}_{y}\cdot zH_2O \qquad (I)$$

where $M^{II}$ is at least one of magnesium, calcium, lanthanum and cerium;

$M^{III}$ is at least iron(III);

$M^{III}$ is at least one n-valent anion; x=Σny; 0<x≤0.67, 0<y≤1, and 0≤z≤10.

4. The dried granular material of claim 1 wherein the mixed metal compound contains at least one of hydroxyl and carbonate ions and contains as the metals iron (III) and magnesium.

5. The dried granular material of claim 1, wherein the excipient comprises a cross-linked disintegrant.

6. The dried granular material of claim 1, wherein the granular material comprises from 5 to 20% by weight of pregelatinised starch as excipient based on the weight of the granule.

7. The dried granular material of claim 1, comprising from 1 to 15% by weight of cross linked polyvinyl pyrrolidone as excipient based on the weight of the granule.

8. The dried granular material of claim 1 wherein the excipient comprises at least pregelatinised starch and crospovidone.

9. The dried granular material of claim 1 wherein at least 95% by weight of the granules of the granular material have a diameter less than 1180 micrometers.

10. A unit dose, comprising:
(i) at least 50% by weight based on the weight of the granule of solid water-insoluble inorganic mixed metal compound capable of binding phosphate and which contains iron (III) and at least one of magnesium, calcium, lanthanum or cerium,
(ii) an excipient, present in an amount no greater than 47% by weight based on the weight of the granule, wherein the mixed metal compound is not hydrothermally treated,
wherein the mixed metal compound has a weight mean particle diameter (d50) in a range of 1 to 20 micrometers.

11. The unit dose of claim 10 wherein the mixed metal compound comprises a layered double hydroxide.

12. The unit dose of claim 10, wherein the mixed metal compound is of formula (I):

$$M^{II}_{1-x} \cdot M^{III}_{x}(OH)_2 A^{n-}_{y} \cdot zH_2O \quad (I)$$

where $M^{II}$ is at least one of magnesium, calcium, lanthanum and cerium;
$M^{III}$ is at least iron(III);
$A^{n-}$ is at least one n-valent anion; x=Σny; 0<x≤0.67, 0<y≤1, and 0≤z≤10.

13. The unit dose of claim 10, wherein the mixed metal compound contains at least one of hydroxyl and carbonate ions and contains as the metals iron (III) and magnesium.

14. The unit dose of claim 10, wherein the excipient comprises a cross-linked disintegrant.

15. The unit dose of claim 10, wherein the granular material comprises from 5 to 20% by weight of pregelatinised starch as excipient based on the weight of the unit dose.

16. The unit dose of claim 10, comprising from 1 to 15% by weight of cross linked polyvinyl pyrrolidone as excipient based on the weight of the unit dose.

17. The unit dose of claim 10, wherein the excipient comprises at least pregelatinised starch and crospovidone.

18. The unit dose of claim 10, further comprising from 3 to 10% by weight based on the weight of the unit dose of non-chemically bound water.

19. The unit dose of claim 10, wherein the unit dose is capsule or a tablet.

* * * * *